(12) United States Patent
Zhu et al.

(10) Patent No.: US 12,295,687 B2
(45) Date of Patent: May 13, 2025

(54) ENDOSCOPE MASTER-SLAVE MOTION CONTROL METHOD AND SURGICAL ROBOT SYSTEM

(71) Applicant: Peking Union Med. College Hosp., Chinese Acad. of Med. Sci. and Peking Union Med. College, Beijing (CN)

(72) Inventors: Lan Zhu, Beijing (CN); Dawei Sun, Beijing (CN); Chang Ren, Beijing (CN)

(73) Assignee: PEKING UNION MEDICAL COLLEGE HOSPITAL, CHINESE ACADEMY OF MEDICAL SCIENCES AND PEKING UNION MEDICAL COLLEGE, Beijing (CN)

( * ) Notice: Subject to any disclaimer, the term of this patent is extended or adjusted under 35 U.S.C. 154(b) by 164 days.

(21) Appl. No.: 18/050,858

(22) Filed: Oct. 28, 2022

(65) Prior Publication Data
US 2024/0115338 A1  Apr. 11, 2024

(30) Foreign Application Priority Data

Oct. 11, 2022  (CN) .......................... 202211241828.7

(51) Int. Cl.
*A61B 34/37* (2016.01)
*A61B 1/00* (2006.01)
(Continued)

(52) U.S. Cl.
CPC ............ *A61B 34/37* (2016.02); *A61B 1/0005* (2013.01); *A61B 1/00087* (2013.01);
(Continued)

(58) Field of Classification Search
CPC .................. A61B 34/37; A61B 1/0005; A61B 1/00087; A61B 1/00181; A61B 1/05; A61B 34/10;
(Continued)

(56) References Cited

U.S. PATENT DOCUMENTS

| 5,855,583 | A | * | 1/1999 | Wang | A61B 34/35 606/139 |
| 6,007,550 | A | * | 12/1999 | Wang | A61B 34/71 606/139 |
| 6,259,806 | B1 | * | 7/2001 | Green | H04N 13/341 348/E13.016 |
| 6,424,885 | B1 | * | 7/2002 | Niemeyer | A61B 34/77 600/109 |

(Continued)

*Primary Examiner* — Jaime Figueroa
(74) *Attorney, Agent, or Firm* — HSML P.C.

(57) ABSTRACT

The present disclosure relates to the field of medical instruments, disclosing an endoscope master-slave motion control method. The endoscope includes an operating arm, a main body disposed at an end of the operating arm, a first imaging unit, a second imaging unit, and an end instrument protruding from a distal end of the main body. The method comprises: determining a current pose of a master manipulator; based on the current pose of the master manipulator and a pose relationship between the master manipulator and the end of the operating arm, determining a target pose of the end of the operating arm; based on the target pose, generating a drive instruction for driving the end of the operating arm; obtaining a first image from the first imaging unit; obtaining a second image from the second imaging unit, wherein the first image and the second image have different fields of view and include images of the end instrument; based on the first and second images, generating a composite scene image to remove an actual image of the end instrument; and generating a virtual image of the end instrument in the composite scene image.

20 Claims, 13 Drawing Sheets

(51) Int. Cl.

| | |
|---|---|
| *A61B 1/05* | (2006.01) |
| *A61B 34/00* | (2016.01) |
| *A61B 34/10* | (2016.01) |
| *A61B 34/20* | (2016.01) |
| *A61B 34/32* | (2016.01) |
| *A61B 90/00* | (2016.01) |
| *G06T 11/60* | (2006.01) |
| *A61B 34/30* | (2016.01) |

(52) U.S. Cl.
CPC ............ *A61B 1/00181* (2013.01); *A61B 1/05* (2013.01); *A61B 34/10* (2016.02); *A61B 34/20* (2016.02); *A61B 34/32* (2016.02); *A61B 34/74* (2016.02); *A61B 90/06* (2016.02); *G06T 11/60* (2013.01); *A61B 2034/102* (2016.02); *A61B 2034/2059* (2016.02); *A61B 2034/301* (2016.02); *A61B 2090/061* (2016.02); *G06T 2210/41* (2013.01)

(58) Field of Classification Search
CPC ......... A61B 34/20; A61B 34/32; A61B 34/74; A61B 90/06; A61B 2034/102; A61B 2034/2059; A61B 2034/301; A61B 2090/061; A61B 90/361; A61B 2034/2065; A61B 2090/306; A61B 2090/309; A61B 2090/371; A61B 1/00009; A61B 1/00149; A61B 1/0016; A61B 1/00193; A61B 34/30; A61B 1/00097; A61B 1/00133; A61B 1/045; A61B 1/0684; A61B 1/07; A61B 1/313; A61B 2034/2072; A61B 2034/305; G06T 11/60; G06T 2210/41
USPC ................. 700/245–264; 318/568.11–568.25
See application file for complete search history.

(56) References Cited

U.S. PATENT DOCUMENTS

| | | | | |
|---|---|---|---|---|
| 6,587,750 B2 * | 7/2003 | Gerbi | ..................... | A61B 34/70 600/595 |
| 6,659,939 B2 * | 12/2003 | Moll | ..................... | A61B 34/35 600/102 |
| 6,728,599 B2 * | 4/2004 | Wang | ..................... | A61B 34/70 600/595 |
| 6,772,053 B2 * | 8/2004 | Niemeyer | .......... | A61B 1/00149 348/E13.016 |
| 7,107,124 B2 * | 9/2006 | Green | ..................... | A61B 34/72 700/262 |
| 7,155,315 B2 * | 12/2006 | Niemeyer | .............. | A61B 34/70 382/128 |
| 7,155,316 B2 * | 12/2006 | Sutherland | ............. | A61B 34/37 901/1 |
| 8,005,571 B2 * | 8/2011 | Sutherland | ............. | A61B 34/37 318/568.22 |
| 8,452,447 B2 * | 5/2013 | Nixon | .................. | A61B 90/361 700/262 |
| 9,770,300 B2 * | 9/2017 | Kwon | ........................ | B25J 3/04 |
| 9,901,408 B2 * | 2/2018 | Larkin | ............... | A61B 1/00193 |
| 10,603,127 B2 * | 3/2020 | Hasser | ................ | A61B 8/4245 |
| 11,896,330 B2 * | 2/2024 | Castillo | ............... | A61B 34/37 |
| 2007/0021738 A1 * | 1/2007 | Hasser | .................... | A61B 34/37 606/1 |
| 2009/0036902 A1 * | 2/2009 | DiMaio | .................... | A61B 8/12 606/130 |
| 2013/0321602 A1 * | 12/2013 | Hayama | ............... | A61B 1/0655 348/68 |
| 2015/0066051 A1 * | 3/2015 | Kwon | .................... | A61B 34/76 606/130 |
| 2016/0235486 A1 * | 8/2016 | Larkin | .................... | A61B 34/20 |
| 2017/0128145 A1 * | 5/2017 | Hasser | .................... | A61B 8/4245 |
| 2018/0036090 A1 * | 2/2018 | Hasegawa | ............. | A61B 34/74 |
| 2018/0042680 A1 * | 2/2018 | DiMaio | .................... | G16H 20/40 |
| 2023/0172438 A1 * | 6/2023 | Usui | .................... | A61B 34/25 606/1 |

\* cited by examiner generate, based on the first image and/or the second image, an actual scene image to display an actual image of the end instrument — 901 display, in response to a display mode instruction, the composite scene image with the virtual image and/or the actual scene image — 903

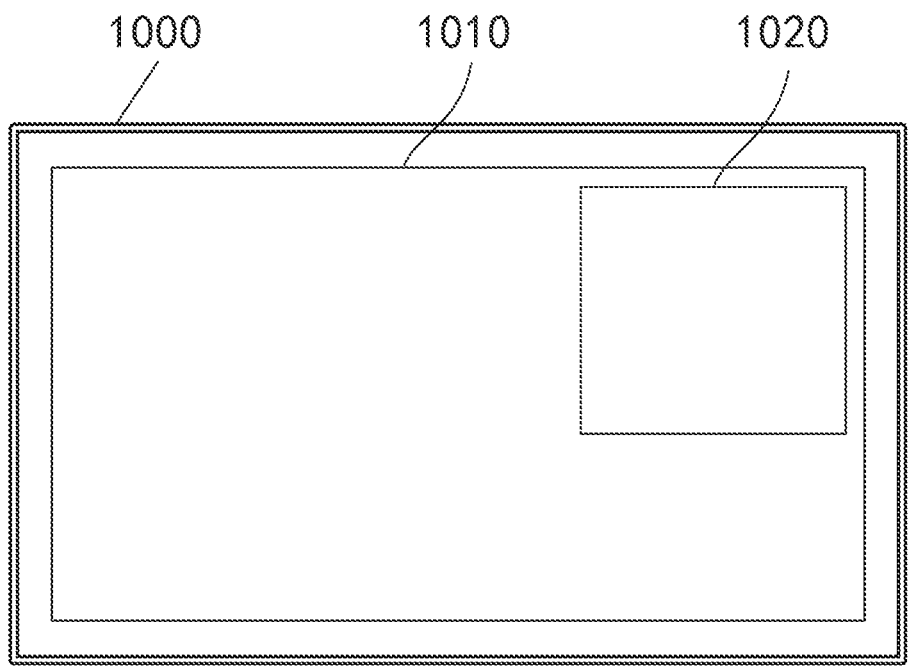

- determine a supplementary image based on the first image or the second image, wherein the supplementary image includes a portion of the second image or the first image that is blocked by the end instrument ~1101
- determine a first environment image or a second environment image based on the first image or the second image, wherein the first environment image and the second environment image do not include the image of the end instrument ~1103
- stitch the first environment image or the second environment image and the supplementary image to generate a stitched image ~1105

1201 — for at least one of the first environment image, the second environment image, the supplementary image or the stitched image, determine an optical flow field of the image based on the image and a previous frame image of the image, wherein the optical flow field comprises optical flows of a plurality of pixels in the image 1203 — generate a depth map of the image based on the optical flow field of the image and a pose of the imaging unit corresponding to the image, wherein the depth map comprises depths of object points corresponding to the plurality of pixels 1205 — determine object point spatial coordinates of the object points corresponding to the plurality of pixels based on the depth map of the image and pixel coordinates of the plurality of pixels 1207 — obtain color information of the plurality of pixels based on the image 1209 — perform a point cloud fusion on the image based on the color information of the plurality of pixels and the object point spatial coordinates, to generate a three-dimensional point cloud

FIG. 12

ENDOSCOPE MASTER-SLAVE MOTION CONTROL METHOD AND SURGICAL ROBOT SYSTEM

TECHNICAL FIELD

The present disclosure relates to the field of medical instruments, and in particular to an endoscope master-slave motion control method and surgical robot system.

BACKGROUND

A modern minimally invasive surgery requires using a surgical robot system with an endoscope for surgical operations. The surgical robot system for remote operations includes a master manipulator for operation and an endoscope for taking images inside a cavity under control of the master manipulator. In an actual scene, the endoscope is configured to include an operating arm controlled by the master manipulator. An operator controls the operating arm to extend into the cavity by remotely operating the master manipulator, and then takes the images through an imaging unit disposed on the endoscope. Sometimes, in order to improve an integration of the surgical robot system, an end instrument is also integrated into the endoscope to juggle image acquisitions and surgical operations.

A surgical robot has a high requirement for operation accuracy and human-computer interaction experience. During a remote operation, it is necessary to provide the operator with a image corresponding to an operation instruction to help the operator perform the surgical operation according to a condition inside the cavity without affecting a field of view, thereby improving an operation experience of the operator.

SUMMARY OF THE INVENTION

In some embodiments, the present disclosure provides an endoscope master-slave motion control method. The endoscope includes an operating arm, a main body disposed at an end of the operating arm, a first imaging unit, a second imaging unit, and an end instrument protruding from a distal end of the main body. The method may include: determining a current pose of the master manipulator; determining, based on the current pose of the master manipulator and a pose relationship between the master manipulator and the end of the operating arm, a target pose of the end of the operating arm; generating, based on the target pose, a drive instruction for driving the end of the operating arm; obtaining a first image from the first imaging unit; obtaining a second image from the second imaging unit, wherein the first image and the second image have different fields of view and include images of the end instrument; generating, based on the first and second images, a composite scene image to remove an actual image of the end instrument; and generating a virtual image of the end instrument in the composite scene image.

In some embodiments, the present disclosure provides a robot system comprising: a master manipulator including a robotic arm, a handle disposed on the robotic arm and at least one master manipulator sensor disposed at at least one joint of the robotic arm, wherein the at least one master manipulator sensor is used for obtaining joint information of the at least one joint; an endoscope including an operating arm, a main body disposed at an end of the operating arm, a first imaging unit, a second imaging unit, and an end instrument protruding from a distal end of the main body; at least one drive device for driving the operating arm; at least one drive device sensor coupled to the at least one drive device and for obtaining status information of the at least one drive device; a control device configured to be connected with the master manipulator, the at least one drive device, the at least one drive device sensor and the endoscope, and to perform the method of any of some embodiments of the present disclosure; and a display device for displaying an image based on a instruction output by the control device.

In some embodiments, the present disclosure provides a computer device comprising: a memory for storing at least one instruction; and a processor coupled with the memory and for executing the at least one instruction to perform the method of any of some embodiments of the present disclosure.

In some embodiments, the present disclosure provides a computer-readable storage medium for storing at least one instruction that when executed by a computer, causes the computer to perform the method of any of some embodiments of the present disclosure.

BRIEF DESCRIPTION OF THE DRAWINGS

In order to explain the technical solutions in the embodiments of the present disclosure more clearly, the accompanying drawings used in the description of the embodiments of the present disclosure will be briefly introduced below. The accompanying drawings in the following description only show some of the embodiments of the present disclosure, and for those of ordinary skill in the art, other embodiments would also have been obtained from the contents of the embodiments of the present disclosure and these accompanying drawings without involving any inventive effort.

FIG. 7A and FIG. 7B show coordinate system schematic diagrams of a robot system according to some embodiments of the present disclosure, wherein FIG. 7A is a coordinate system schematic diagram in a master-slave motion mapping, and FIG. 7B is a coordinate system schematic diagram of the endoscope;

FIG. 10 shows a schematic diagram of a multi-scene display on a display device according to some embodiments of the present disclosure;

FIG. 11 shows a flowchart of a method of generating a composite scene image based on a first image and a second image according to some embodiments of the present disclosure;

FIG. 12 shows a flowchart of a method of generating a three-dimensional composite scene image based on a first image and a second image according to some embodiments of the present disclosure;

DETAILED DESCRIPTION

Figure 1:
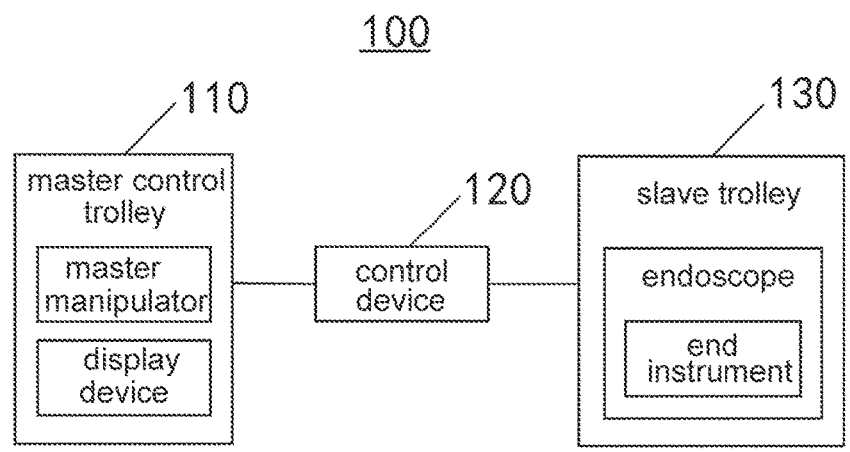
FIG. 1 shows a structure block diagram of a robot system according to some embodiments of the present disclosure.

To make the solved technical problems, used technical solutions, and achieved technical effects of the present disclosure more clearly, the technical solutions of the embodiments of the present disclosure will be further described in detail below with reference to the accompanying drawings. Obviously, the described embodiments are only exemplary embodiments, but not all of embodiments, of the present disclosure.

In the description of the present disclosure, it should be noted that, orientational or positional relationships indicated by the terms "center", "upper", "lower", "left", "right", "vertical", "horizontal", "inner", "outer" and the like are the orientational or positional relationships shown based on the accompanying drawings, and are only for ease of describing the present disclosure and simplifying the description, rather than indicating or implying that the apparatus or element referred to must have a specific orientation or be constructed and operated in a specific orientation, and therefore cannot be construed as limiting the present disclosure. In addition, the terms "first" and "second" are used for descriptive purposes only, and cannot be understood as indicating or implying relative importance. In the description of the present disclosure, it should be noted that, unless otherwise specified and defined, the term "mount", "connected", and "connect", or "couple" should be comprehended in a broad sense. For example, the term may be a fixed connection or a detachable connection; or may be a mechanical connection or an electrical connection; may be a direct connection or an indirect connection via an intermediate medium; or may be internal communication between two elements. For those of ordinary skill in the art, specific meanings of the foregoing terms in the present disclosure may be understood based on specific situations.

In the present disclosure, an end close to an operator (e.g., a surgeon) is defined as a proximal end, a proximal portion, a rear end, or a rear portion, and an end close to a patient who requires surgery is defined as a distal end, a distal portion, a front end, or a front portion. It may be understood that the embodiments of the present disclosure may be used for a medical instrument or a surgical robot, and may also be used for other non-medical apparatus. In the present disclosure, a reference coordinate system may be understood as a coordinate system capable of describing a pose of an object. According to actual positioning requirements, the reference coordinate system may be chosen to take an origin of a virtual reference object or an origin of a real reference object as an origin of the coordinate system. In some embodiments, the reference coordinate system may be a world coordinate system, or a coordinate system of the space where a certain point on a master manipulator, an end of an operating arm, a main body of an endoscope, an end instrument, an imaging unit or a lumen is located, or the operator's own perception coordinate system and the like.

In the present disclosure, the object may be understood as a subject or a target needed to be positioned, such as the operating arm or the end of the operating arm, and may also be a certain point on the lumen. The pose of the operating arm or a portion (e.g., the end) thereof may refer to a pose of a coordinate system defined by the operating arm, a portion of the operating arm or a portion rigidly extending on the operating arm (e.g., the main body of the endoscope or the end instrument) relative to the reference coordinate system.

FIG. 1 shows a structure block diagram of a robot system 100 according to some embodiments of the present disclosure. In some embodiments, as shown in FIG. 1, the robot system 100 may include a master control trolley 110, a slave trolley 130 and a control device 120. The control device 120 may be communicatively connected with the master control trolley 110 and the slave trolley 130, for example, via cable connections, or via wireless connections, to achieve the communication with the master control trolley 110 and the slave trolley 130. The master control trolley 110, which functions as an operating terminal and an interacting terminal of the robot system 100, may include a master manipulator for an operator to operate remotely, and a display device for displaying an image of an operating area. The slave trolley 130, which functions as a working terminal of the robot system 100, includes an endoscope for taking images and performing tasks. With the control device 120 to achieve the master-slave mapping between the master manipulator in the master control trolley 110 and the endoscope in the slave trolley 130, the motion control of the endoscope by the master manipulator is achieved. In some embodiments, a distal portion of the endoscope is provided to be able to enter into the operating area via a lumen through a tube sleeve, a sheath sleeve, etc., photograph a target area in the scene and generate a two-dimensional or three-dimensional scene image to be displayed on the display device. The endoscope may include an end instrument disposed at its distal end, and the end instrument may be a surgical tool, for example, a clamp-type device, a hemostatic device, a drug delivery device, etc. In some embodiments, the robot system 100 may be configured to be capable of processing the captured scene image to generate multiple images such as a composite scene image comprising an actual scene image of the end instrument and/or comprising a virtual image of the end instrument, and selectively display these images on the display device based on an instruction (for example, a display mode instruction). By controlling the robot system 100, it is possible to operate the end instrument to, at a surgical site, perform surgical tasks on an object (e.g., pathological tissue, etc.) to be operated in a contact or non-contact way in the case of obtaining the field of view of the operating area and the surgical site. The tube sleeve and the sheath sleeve may be fixed to human or animal body etc., forming an opening (for example an incision or a natural opening), the lumen may be the trachea, esophagus, vagina, intestine, etc., the operating area may be the area where the surgical tasks are performed, and the scene may be the lumen or the operating area. Those skilled in the art will appreciate that the master control trolley 110 and the slave trolley 130 may employ other structures or forms, such as a base, a bracket or a building and the like. The master control trolley 110 and the slave trolley 130 may also be integrated on the same device.

Figure 2:
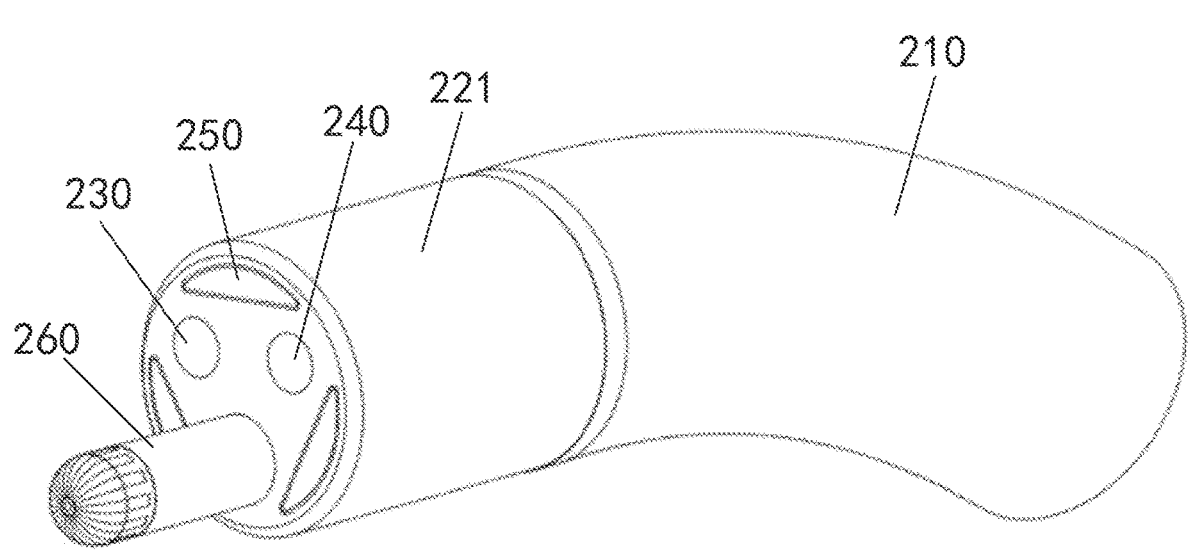
FIG. 2 shows a structure diagram of an endoscope according to some embodiments of the present disclosure.
Figure 3:
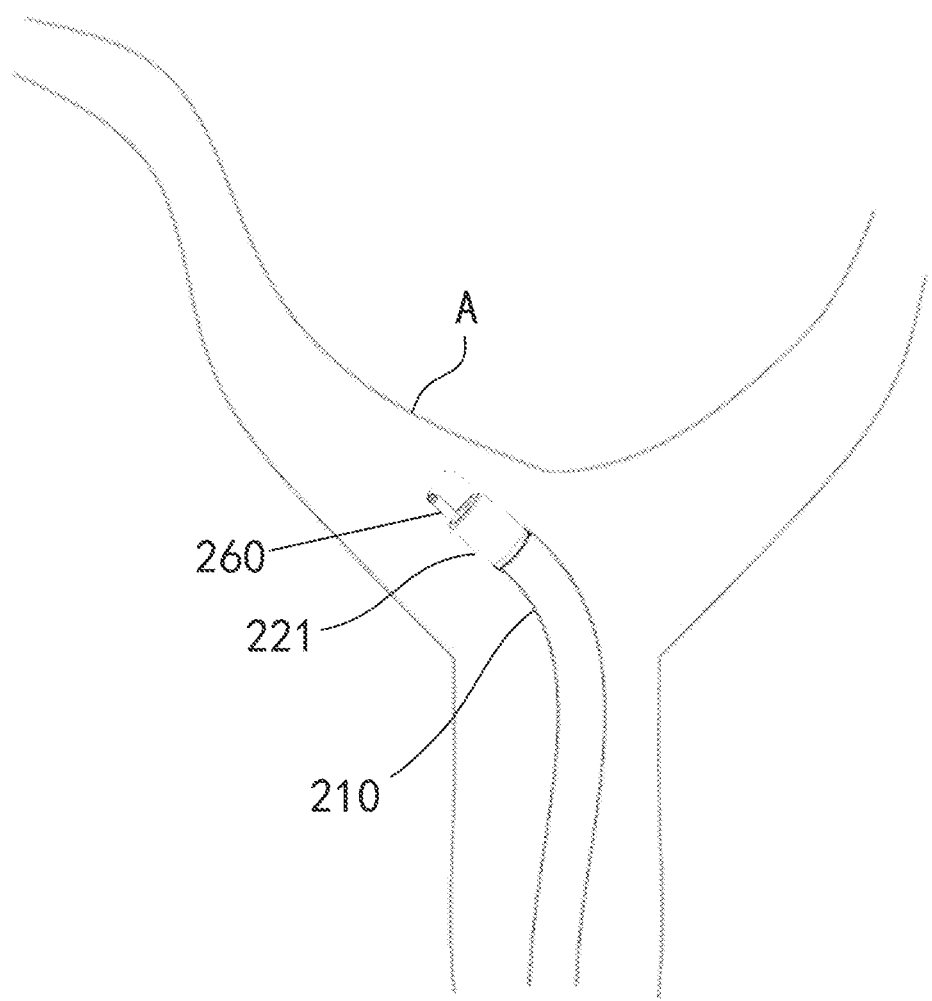
FIG. 3 shows a structure diagram of the endoscope located within an internal lumen according to some embodiments of the present disclosure.

FIG. 2 shows a structure diagram of an endoscope 200 according to some embodiments of the present disclosure. FIG. 3 shows a structure diagram of the endoscope 200 being located within a lumen A in a body (for example in a human body or an animal body) according to some embodiments of the present disclosure. As shown in FIGS. 2 and 3, the endoscope 200 may include an operating arm 210 and an endoscope main body 221. In some embodiments, the operating arm 210 may be a continuum body capable of being bent controllably, may include a segment bendable on at least one degree of freedom at the distal end, and the distal end of the operating arm 210 is provided with the endoscope main body 221. The operating arm 210 may be disposed on the slave trolley 130, and the pose of the master manipulator and the pose of the end of the operating arm have a master-slave motion mapping relationship. In some embodiments, the operating arm may change the steering of the endoscope main body 221 based on operating instructions issued by a operator to avoid vital organs within the body or to adapt to the complex curved lumen A, so that the endoscope main body 221 feeds into the operating area through the lumen A or withdraw from the lumen A. In some embodiments, the operating arm may adjust the pose of the endoscope main body 221 based on the operating instructions, so as to facilitate an imaging unit (e.g., a first imaging unit 230 and a second image unit 240 shown in FIG. 2 and FIG. 3, a first imaging unit 430 and a second imaging unit 440 shown in FIG. 4, or a first imaging unit 1761 and a second imaging unit 1762 shown in FIG. 17) on the endoscope main body 221 to photograph the operating area, and to enable an end instrument (e.g., an end instrument 260 shown in FIG. 2 and FIG. 3, an end instrument 460 shown in FIG. 4, or an end instrument 1765 shown in FIG. 17) on the endoscope main body 221 to align with the surgical site in the operating area.

The endoscope 200 may further include the first imaging unit 230, the second imaging unit 240, and the end instrument 260. In some embodiments, the endoscope 200 may further include at least one illumination unit 250. As shown in FIG. 2, the endoscope main body 221 may be in a roughly columnar shape, its cross-sectional shape may be circular or oval to meet different functional needs.

The first imaging unit 230 may be used to take a first image, and the second imaging unit 240 may be used to take a second image. In some embodiments, the first imaging unit 230 and the second imaging unit 240 may be, for example, a CCD camera, and comprise a set of image sensors and image lenses, respectively, and the image lens may be disposed at a distal end of the image sensor and align with at least corresponding image sensor, so as to facilitate the image sensor to photograph a target area in the scene through the image lens. In some embodiments, the image lens may include a plurality of convex lenses and concave lenses, and the plurality of convex lenses and concave lenses form an optical imaging system by a distribution arrangement. For example, the distal surface of the image lens may be a curved convex lens, for example a spherical lens, an ellipsoidal lens, a cone lens, a frustum lens, and the like. The image lens may include at least one convex surface to increase a range of the field of view that can be photographed.

The illumination unit 250 is used to provide illumination, so as to facilitate the photographing of the first imaging unit 230 and the second imaging unit 240. As shown in FIG. 2, in some embodiments, three illumination units 250 are provided along a perimeter edge of the endoscope 200, located between two imaging units or between an imaging unit and the end instrument 260, respectively, but not limited thereto. The number and arrangement mode of illumination units 250 may be changed according to actual needs. For example, the number of illumination units 250 may also be two, located on the left and right sides of the endoscope 200. Alternatively, in order to further increase the illumination intensity, the number of illumination units 250 may also be greater than three. In some embodiments, the cross-section of the illumination unit 250 may be crescent-shaped, thereby making full use of the space on the endoscope 200, facilitating to achieve miniaturization of the endoscope and increase the field of view of illumination. However, the shape of the cross-section of the illumination unit 250 is not limited thereto, and the illumination unit 250 may also be in other shapes. In some embodiments, the illumination unit 250 may include a light source and one or more fibers coupled to the light source. In the interior of the endoscope main body 221, an illumination channel may be formed for disposing the fiber. In some embodiments, the light source of the illumination unit 250 may be, for example, an LED light source.

In some embodiments, the end instrument 260 may be configured to protrude from the distal end of the endoscope main body 221 to perform surgical tasks, as described below in detail. In some embodiments, the endoscope 200 may further include a ranging unit (not shown in the figure) for measuring the distance between the endoscope 200 and the surgical site. The ranging unit may be a ranging sensor, for example, a laser ranging sensor and the like. By disposing the ranging unit, the distance between the endoscope 200 (e.g., the distal surface of the endoscope main body 221) and the operating site can be determined, thereby the distance between the end instrument 260 and the operating site can be determined.

Figure 4:
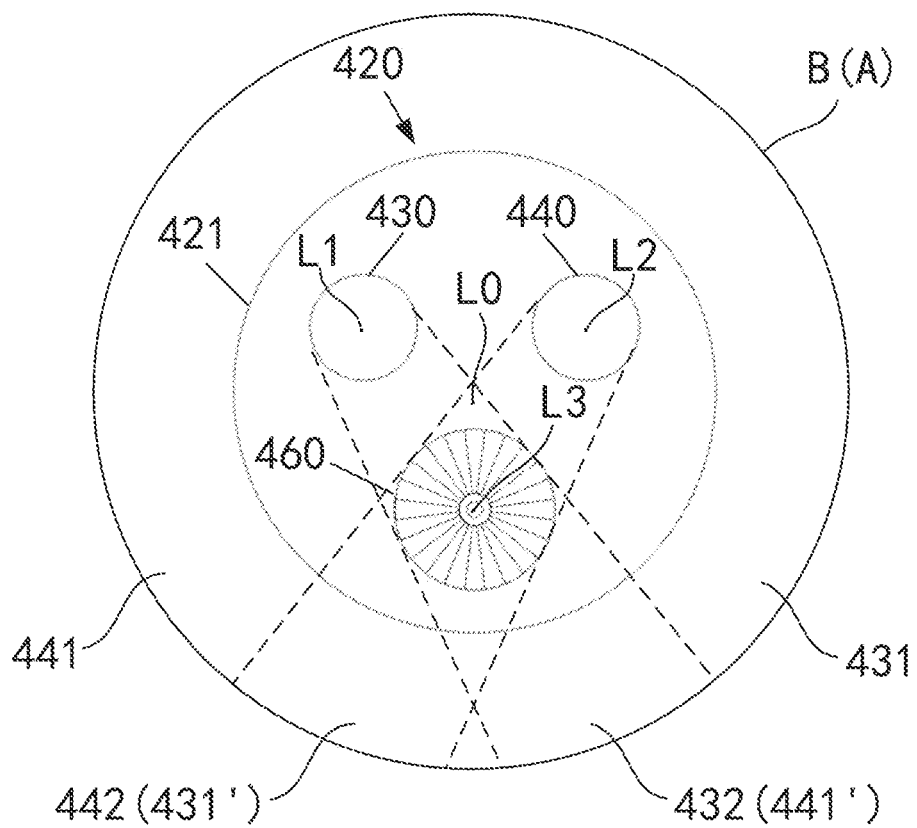
FIG. 4 shows a schematic diagram of relative positional relationships between a first imaging unit, a second imaging unit and an end instrument according to some embodiments of the present disclosure.

FIG. 4 shows a schematic diagram of relative positional relationships between a first imaging unit 430, a second imaging unit 440 and an end instrument 460 according to some embodiments of the present disclosure. As shown in FIG. 4, in some embodiments, the first imaging unit 430 may be configured to be located on one side of the endoscope main body 421 with respect to the end instrument 460, and has a first field of view corresponding to the orientation of its own optical axis L1.

It should be understood that the first field of view of the first imaging unit 430 is formed as a roughly conical shape centered on the optical axis L1. FIG. 4 schematically shows a cross-section of the first field of view, a plane where the cross-section is located is perpendicular to the optical axis L1. Further, it should be understood that a plane where the first imaging unit 430 and the second imaging unit 440 as described below is located, the distal surface of the end instrument 460, the cross-sections of the first field of view and the second field of view as described below are not located in the same plane, but for ease of description, FIG. 4 shows, on the same plane, the plane where the first imaging unit 430 and the second imaging unit 440 as described below is located, the distal surface of the end instrument 460, the cross-sections of the first field of view and the second field of view as described below.

The first field of view includes a field of view 431 and a field of view 432, wherein the field of view 431 is a portion of the first field of view that is not blocked by the end instrument 460, and the field of view 432 is a portion of the first field of view that is blocked by the end instrument 460. As shown in FIG. 4, the range of the field of view 431 and the field of view 432 covers the cross-section of the entire operating area B (or the lumen A). The first imaging unit 430 may take a first image of the operating area B (or the lumen A) in the first field of view, and the first image includes an image of the end instrument 460.

The second imaging unit 440 may be configured to be located on the other side (opposite side) of the endoscope main body 421 with respect to the end instrument 460, and has a second field of view corresponding to the orientation of its own optical axis L2. Similar to the first imaging unit 430, the second field of view of the second imaging unit 440 is formed as a roughly conical shape centered on the optical axis L2. FIG. 4 schematically shows a cross-section of the second field of view, a plane where the cross-section is located is perpendicular to the optical axis L2. The second field of view includes a field of view 441 and a field of view 442, wherein the field of view 441 is a portion of the second field of view that is not blocked by the end instrument 460, and the field of view 442 is a portion of the second field of view that is blocked by the end instrument 460. As shown in FIG. 4, the range of the field of view 441 and the field of view 442 covers the cross-section of the entire operating area B (or the lumen A). The second imaging unit 440 may take a second image of the operating area B (or the lumen A) in the second field of view, and the second image has a different field of view from that of the first image and includes an image of the end instrument 460.

In some embodiments, the optical axis L1 of the first imaging unit 430 and the optical axis L2 of the second imaging unit 440 may be parallel to an axis L0 of the endoscope main body 421, respectively, and an axis L3 of the end instrument 460 may be parallel to the axis L0 of the endoscope main body 421 and deviate from a connecting line between the first imaging unit 430 and the second imaging unit 440. For example, the first imaging unit 430, the second imaging unit 440 and the end instrument 460 may be configured such that the optical axis L1 of the first imaging unit 430, the optical axis L2 of the second imaging unit 440 and the axis L3 of the end instrument 460 are perpendicular to the distal surface of the endoscope main body 421, respectively, the first imaging unit 430 and the second imaging unit 440 are symmetrically arranged with respect to the end instrument 460, and the axis L3 of the end instrument 460 is located below the connecting line between the first imaging unit 430 and the second imaging unit 440. By configuring the optical axes of the first imaging unit 430 and the second imaging unit 440 to be parallel to each other, and arranging the first imaging unit 430 and the second imaging unit 440 symmetrically on both sides of the end instrument 460, it can be achieved that the first image captured by the first imaging unit 430 and the second image captured by the second imaging unit 440 are symmetrical with each other, thereby facilitating to the processing of the first image and the second image, improving a picture generation quality and a picture processing speed of the robot system.

Those skilled in the art will appreciate that, although in the present disclosure, for ease of description, the first image and the second image are described as examples, the embodiments of the present disclosure may be applied to the processing of a sequence of first images and a sequence of second images, to form continuous video frame processing and displaying. Thus, the capturing, processing and displaying of the sequence of first images and the sequence of second images fall within the scope of the present disclosure and fall within the scope of protection of the claims of the present disclosure.

In the present disclosure, the end instrument (e.g., the end instrument 260 shown in FIG. 2 and FIG. 3, the end instrument 460 shown in FIG. 4, or the end instrument 1765 shown in FIG. 17) may include a surgical tool, such as a hemostatic device (e.g., an electrocoagulation hemostatic device), a clamp-type device, a drug delivery device and the like, to adapt to different surgical needs. The following describes the end instrument as the electrocoagulation hemostatic device.

In some embodiments, the end instrument may be configured such that its proximal end is fixedly connected to the distal end of the endoscope main body, whereby the pose of the end instrument can be changed by adjusting the pose of the endoscope main body, enabling the end instrument to be aligned to the surgical site in the operating area. In some embodiments, the end instrument may be a bipolar electrocoagulation hemostatic device. For example, the end instrument may include at least one first electrode, at least one second electrode and an insulating body, wherein the at least one first electrode and the at least one second electrode are alternately arranged on a circumferential outward side of the insulating body, at least a portion of the first electrode is exposed, and at least a portion of the second electrode is exposed. When a high-frequency current is turned on, at least the exposed portion of the first electrode and at least the exposed portion of the second electrode form a circuit for electrocoagulation hemostasis.

Figure 5:
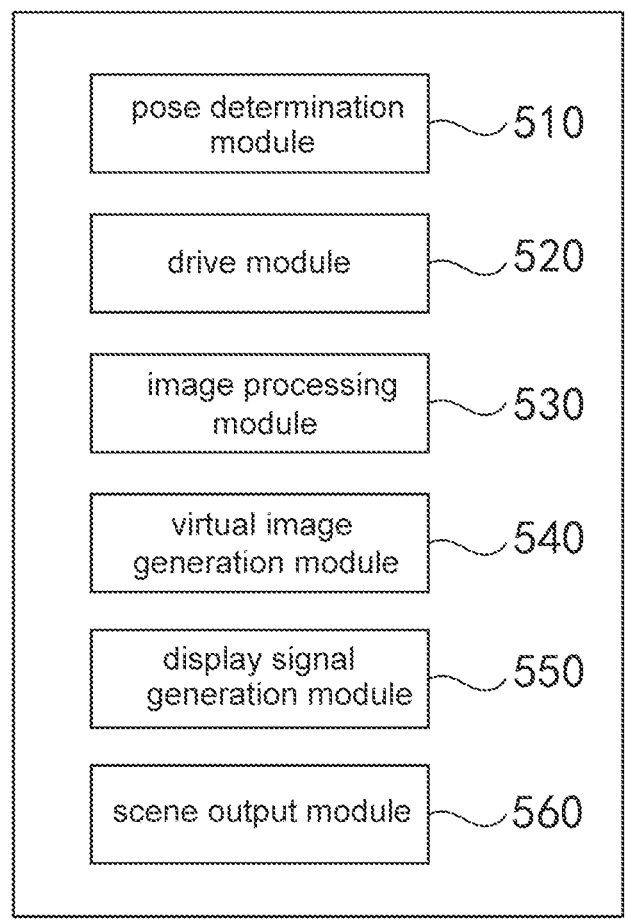
FIG. 5 shows a schematic block diagram of a control device according to some embodiments of the present disclosure.

FIG. 5 shows a structural block diagram of a control device 500 according to some embodiments of the present disclosure. The control device 500 is used to achieve the control of the endoscope based on an endoscope master-slave motion control method. As shown in FIG. 5, the control device 500 may include a pose determination module 510, a drive module 520, an image processing module 530, a virtual image generation module 540, a display signal generation module 550 and a scene output module 560. The pose determination module 510 may be used to determine a pose of the endoscope 200. In some embodiments, the pose determination module 510 may determine a target pose of an end of the operating arm 210 based on a current pose of the master manipulator, and further determine poses of the endoscope main body 221 and the first imaging unit 230, the second imaging unit 240 and the end instrument 260 disposed on the endoscope main body 221. The drive module 520 is to generate a drive instruction to drive the operating arm 210. In some embodiments, the drive module 520 may generate the drive instruction for driving the end of the operating arm 210 based on the target pose of the end of the operating arm 210. The image processing module 530 may be configured to receive a first image from the first imaging unit (e.g., the first imaging unit 230 shown in FIG. 2, the first imaging unit 430 shown in FIG. 4 or the first imaging unit 1761 shown in FIG. 17) and a second image from the second imaging unit (e.g., the second imaging unit 240 shown in FIG. 2, the second imaging unit 440 shown in FIG. 4 or the second imaging unit 1762 shown in FIG. 17), and generate a composite scene image and an actual scene image based on the first image and the second image. In some embodiments, the image processing module 530 may generate a scene image with depth information based on a pose change of the first imaging unit 230 and the second imaging unit 240 on the endoscope main body 221. The details will be described later. The virtual image generation module 540 may be used to generate a virtual image of the end instrument (e.g., the end instrument 260 shown in FIG. 2 and FIG. 3, the end instrument 460 shown in FIG. 4, or the end instrument 1765 shown in FIG. 17) in the composite scene image. The display signal generation module 550 is to generate a display signal based on a display mode instruction. In some embodiments, the display mode instruction is used to switch the display mode of the image based on the operator's operation (e.g., controlling a motion of the endoscope or controlling an operation of the end instrument or selecting the display mode). The scene output module 560 may, based on the display signal, switch to output the composite scene image with the virtual image or the actual scene image to the display device, or output the composite scene image with the virtual image and the actual scene image to the display device simultaneously. It should be understood that the control device of the present disclosure includes, but is not limited to, the above structures; any of the control devices that can implement the control of the robot system does not depart from the scope of the present disclosure.

In some embodiments, the display device of the robot system 100 may display an image based on the instruction output by the control device. The imaging unit (e.g., the first imaging unit 230 and the second imaging unit 240 shown in FIG. 2, the first imaging unit 430 and the second imaging unit 440 shown in FIG. 4 or the first imaging unit 1761 and the second imaging unit 1762 shown in FIG. 17) may be used to acquire an image of the operating area, and transmit the acquired image to the control device (e.g., the control device 120 shown in FIG. 1 or the control device 500 shown in FIG. 5). After the image is processed by the image processing module (e.g., the image processing module 530 shown in FIG. 5) in the control device, it is displayed on the display device. The operator may feel a pose change of the end of the operating arm relative to the reference coordinate system in real time through the image in the display device (for example, the actual scene image or the composite scene image of a wall surface of the lumen). For example, a displacement direction in the image may differ from a direction of a position change of the end of the operating arm relative to the reference coordinate system, and a rotation direction in the image may differ from a direction of an orientation change of the end of the operating arm relative to the reference coordinate system. The pose of the master manipulator relative to the reference coordinate system is a pose that the operator actually perceives. The pose change felt by the operator through a remote operation on the master manipulator and the pose change in the image perceived by the operator in the display device conform to a specific pose relationship. Through the remote operation on the master manipulator, the pose change of the master manipulator is converted into the pose change of the end of the operating arm based on the pose relationship, and then a pose control on the endoscope main body at the end of the operating arm is realized. When the operator holds a handle of the master manipulator to move so as to operate the operating arm, based on a principle of an intuitive operation, the orientation change or position change in the image felt by the operator is kept to be equal or proportional in the change amount to the orientation change of the master manipulator felt by the operator, which facilitates to improve remote operation feeling and remote operation accuracy of the operator.

In the present disclosure, during the remote operation, the endoscope is controlled by the master manipulator to move to a desired position and orientation according to desire of the operator, and the operator is provided with an intracavity image corresponding to the operation instruction and a visual field requirement.

Figure 6:
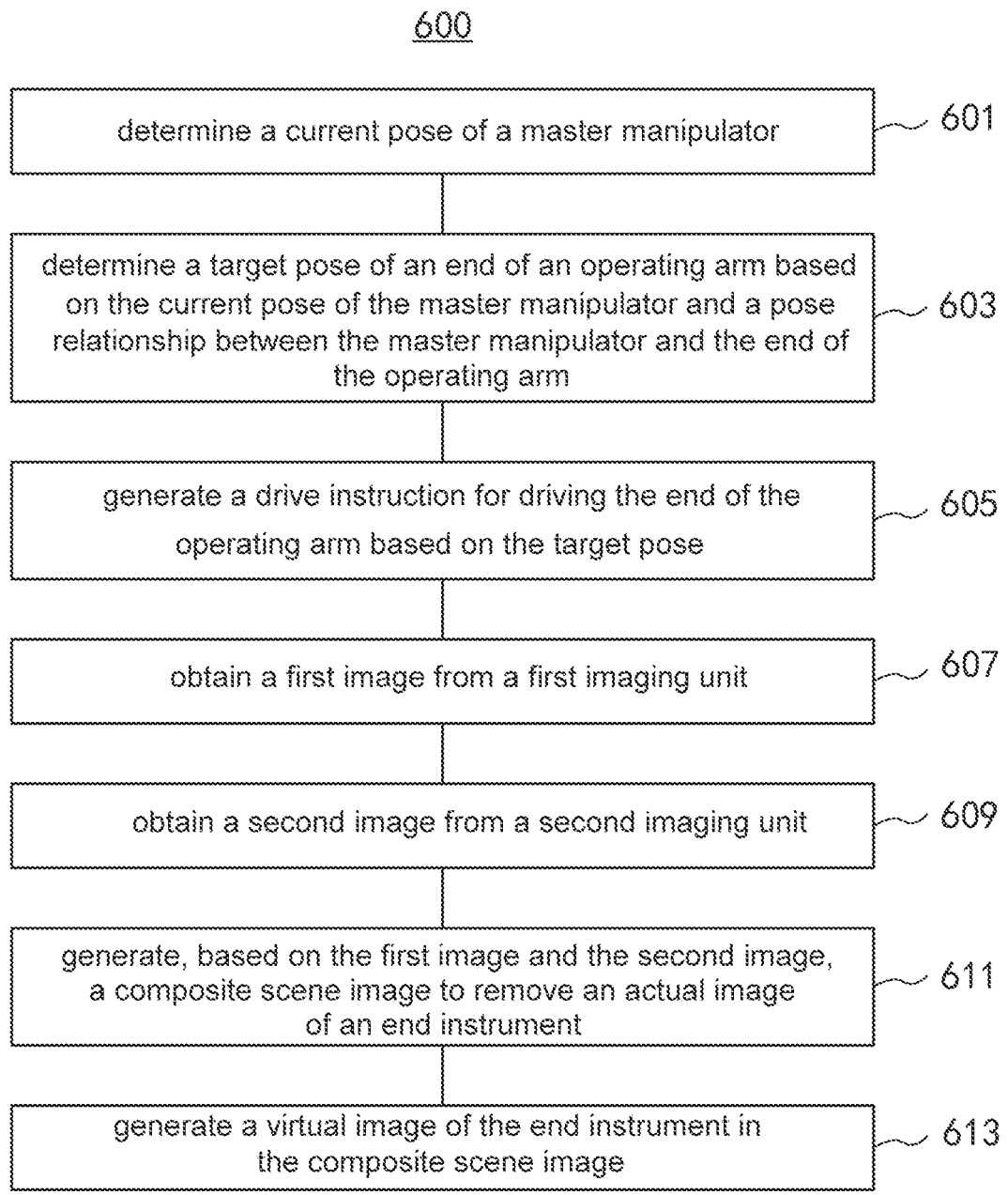
FIG. 6 shows a flowchart of an endoscope master-slave motion control method according to some embodiments of the present disclosure.

Some embodiments of the present disclosure provide an endoscope master-slave motion control method. FIG. 6 shows a flowchart of an endoscope master-slave motion control method 600 according to some embodiments of the present disclosure. In some embodiments, part or all of the steps in the method 600 may be performed by the control device (e.g., the control device 500 shown in FIG. or the control device 1770 shown in FIG. 17) of the robot system (e.g., the robot system 100 shown in FIG. 1 or the robot system 1700 shown in FIG. 17). The control device may include a computing device. The method 600 may be implemented by software, firmware and/or hardware. In some embodiments, the method 600 may be implemented as computer-readable instructions. These instructions may be read and executed by a general-purpose processor or a dedicated processor (e.g., the control device 1770 shown in FIG. 17). In some embodiments, these instructions may be stored on a computer-readable medium.

Figure 7A:
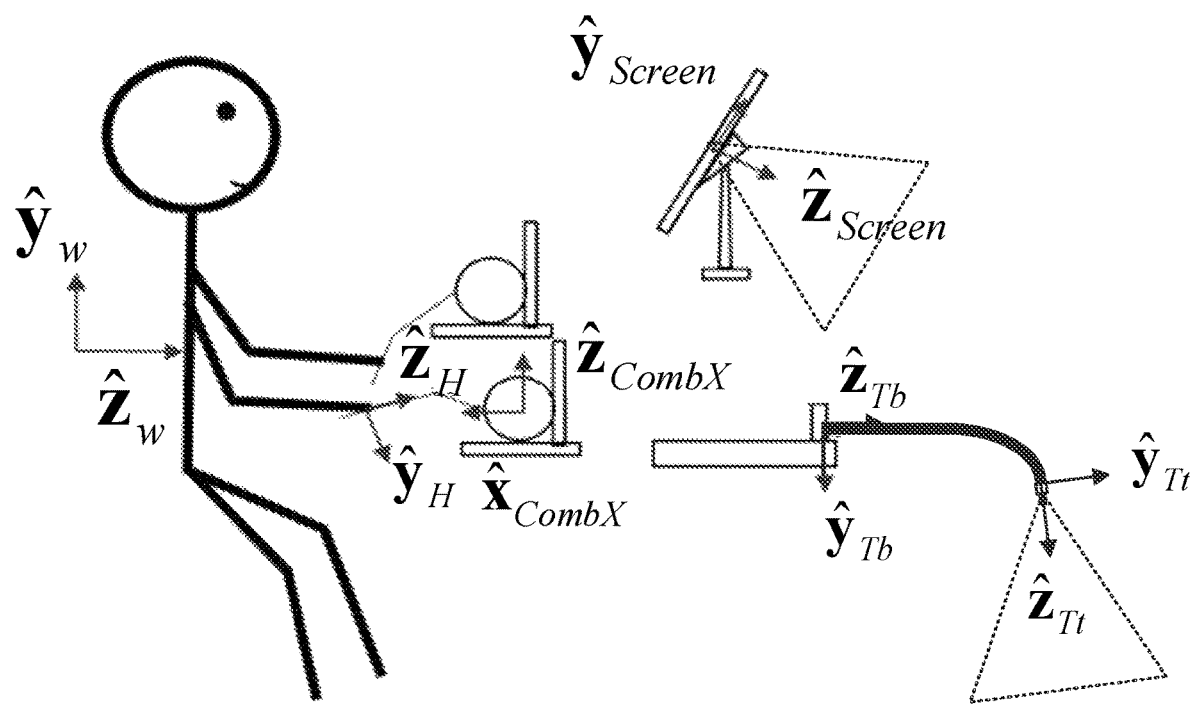
Figure 7B:
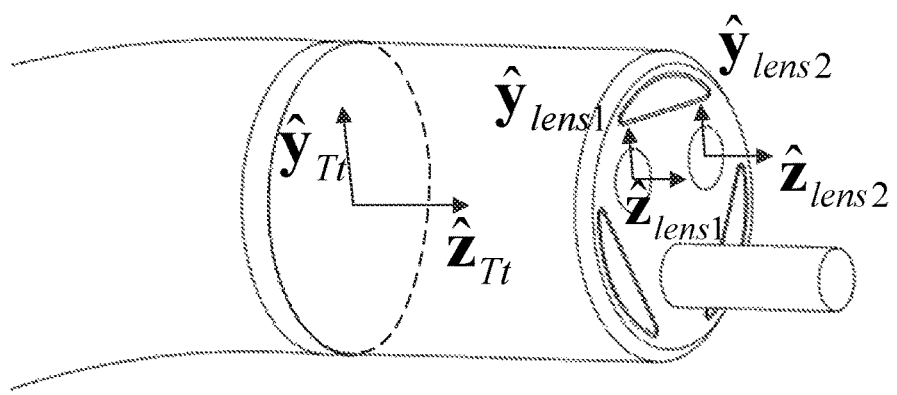

FIG. 7A and FIG. 7B show coordinate system schematic diagrams of a robot system according to some embodiments of the present disclosure, wherein FIG. 7A is a coordinate system schematic diagram in a master-slave motion mapping, and FIG. 7B is a coordinate system schematic diagram of the endoscope. The coordinate systems in FIG. 7A and FIG. 7B are defined as follows: an operating arm base coordinate system {Tb}, in which an origin is located at a base of the operating arm or an exit of a sheath sleeve, $\hat{z}_{Tb}$ is consistent with an extended line of the base or an axial direction of the sheath sleeve, and a direction of $\hat{y}_{Tb}$ is shown as in FIG. 7A. An end coordinate system (Tt) of an operating arm, in which an origin is located at the end of the operating arm, $\hat{z}_{Tt}$ is consistent with an axis direction of the end, and a direction of $\hat{y}_{Tt}$ is shown in FIG. 7A. A reference coordinate system {w}, which may be the coordinate system of the space where the master manipulator or the operating arm of the endoscope is located, for example the operating arm base coordinate system {Tb}, or the world coordinate system, as shown in FIG. 7A. In some embodiments, the operator's somatosensation may be used as a reference. When the operator is sitting upright in front of a main console, a somatosensation upward direction is a direction of $\hat{y}_w$, and a somatosensation forward direction is a direction of $\hat{z}_w$. A master manipulator base coordinate system {CombX}, in which its coordinate axis directions are shown in FIG. 7A. A master manipulator's handle coordinate system {CombX}, in which its coordinate axis directions are shown in FIG. 7A. An imaging unit coordinate system {lens}, in which an origin is located at a center of the imaging unit, an optical axis direction is a direction of $\hat{z}_{lens}$, and an upper direction after the field of view is straightened is a direction of $\hat{y}_{lens}$. In some embodiments, as shown in FIG. 7B, the imaging unit coordinate system (lens) may include a first imaging unit coordinate system (lens1) and a second imaging unit coordinate system {lens2}, in which an optical axis direction of the first imaging unit is a direction of $\hat{z}_{lens1}$, an upper direction after the field of view is straightened is a direction of $\hat{y}_{lens1}$, an optical axis direction of the second imaging unit is a direction of $\hat{z}_{lens2}$, and an upper direction after the field of view is straightened is a direction of $\hat{y}_{lens2}$. A display coordinate system (Screen), in which an origin may be at a center of the display, an inward direction perpendicular to a screen picture is a direction of $\hat{z}_{Screen}$ and a direction above the screen picture is a direction of $\hat{y}_{Screen}$. In some embodiments, the display coordinate system {Screen} may be consistent with the imaging unit coordinate system {lens} in a definition of a direction of the field of view. For example, the display coordinate system {Screen} may be consistent with the first imaging unit coordinate system {lens1} or the second imaging unit coordinate system {lens2} in the definition of the direction of the field of view. Those skilled in the art may understand that a pose of the imaging unit coordinate system {lens} will change with a motion of the end of the operating arm, a field of view displayed on the display will also change accordingly, and a correspondence between the operator's somatosensation direction and a direction of the motion of the end of the operating arm will also change, but the operator's somatosensation coordinate system (e.g., the reference coordinate system {w}) and the imaging unit coordinate system {lens} has a predetermined correspondence. For example, when the operator pushes the master manipulator forward (e.g., in the direction of $\hat{z}_w$), since the display coordinate system {Screen} is consistent with the imaging unit coordinate system {lens} in the definition of the direction of the field of view, the end of the operating arm may be controlled to move in the direction of $\hat{z}_{lens}$. Similarly, in the x and y directions, there is a specific correspondence. In this way, the operator can be provided with an experience of intuitive operation.

The coordinate systems shown in FIGS. 7A and 7B are taken as examples to describe the endoscope master-slave motion control method 600 below. However, those skilled in the art may understand that other coordinate system definitions may be used to implement the endoscope master-slave motion control method 600.

Referring to FIG. 6, at step 601, a current pose of the master manipulator may be determined. The current pose includes a current position and a current orientation. In some embodiments, the current pose of the master manipulator may be a pose relative to the master manipulator base coordinate system {CombX} or the reference coordinate system {w}. For example, the pose of the master manipulator is a pose of a coordinate system {H} defined by the handle or a portion of the master manipulator relative to the master manipulator base coordinate system {CombX} (for example, a coordinate system defined by a bracket or base on which the master manipulator is located, or the world coordinate system). In some embodiments, determining the current position of the master manipulator comprises determining the current position of the handle of the master manipulator relative to the master manipulator base coordinate system {CombX}, and determining the current orientation of the master manipulator comprises determining the current orientation of the handle of the master manipulator relative to the master manipulator base coordinate system {CombX}. In some embodiments, the step 601 may be performed by the control device 500 (e.g., the pose determination module 520).

In some embodiments, the current pose of the master manipulator may be determined based on a coordinate transformation. For example, the current pose of the handle of the master manipulator may be determined based on a transformation relationship between the coordinate system {H} of the handle and the master manipulator base coordinate system {CombX}. In general, the master manipulator base coordinate system {CombX} may be disposed on the bracket or base where the master manipulator is located, and the master manipulator base coordinate system {CombX} remains unchanged during a remote operation. The master manipulator base coordinate system {CombX} may be the same as the reference coordinate system {w} or have a predetermined transformation relationship with the reference coordinate system {w}.

In some embodiments, the current pose of the master manipulator may be determined based on a master manipulator sensor. In some embodiments, current joint information of at least one joint of the master manipulator is received, and based on the current joint information of the at least one joint, the current pose of the master manipulator is determined. For example, the current pose of the master manipulator is determined based on the current joint information of the at least one joint obtained by the master manipulator sensor. The master manipulator sensor is disposed at least one joint position of the master manipulator. For example, the master manipulator includes at least one joint, and at least one master manipulator sensor is disposed at the at least one joint. Based on the master manipulator sensor, the joint information (a position or an angle) of a corresponding joint is obtained, and the current pose of the master manipulator is calculated. For example, the current position and current orientation of the master manipulator are calculated based on a forward kinematics algorithm.

Figures 8, 9:
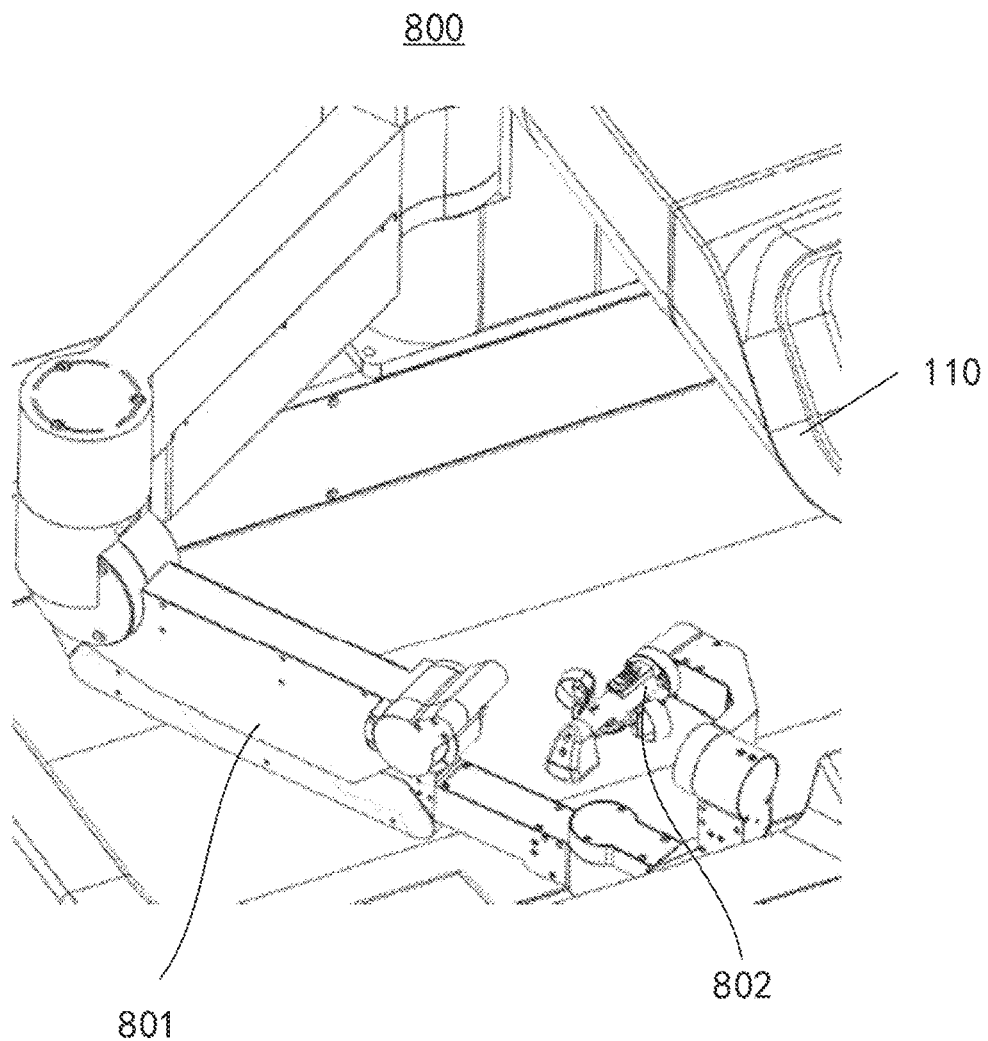
FIG. 8 shows a schematic diagram of a master manipulator according to some embodiments of the present disclosure.
FIG. 9 shows a flowchart of a method of displaying a scene image based on a display mode instruction according to some embodiments of the present disclosure.

In some embodiments, the master manipulator includes at least one orientation joint for controlling the orientation of the handle. Determining the current orientation of the handle of the master manipulator includes: obtaining joint information of the at least one orientation joint, and determining the current orientation of the master manipulator based on the joint information of the at least one orientation joint. FIG. 8 shows a schematic diagram of a master manipulator 800 according to some embodiments of the present disclosure. The master manipulator 800 may be disposed on a master control trolley, for example, the master control trolley 110 shown in FIG. 1 As shown in FIG. 8, the master manipulator 800 includes a robotic arm 801 having multiple degrees of freedom, and the robotic arm 801 includes a position joint and an orientation joint. The orientation joint adjusts an orientation of the master manipulator 800, and a target orientation is reached by controlling the master manipulator 800 through one or more orientation joints. The position joint adjusts a position of the master manipulator 800, and a target position is reached by controlling the master manipulator 800 through one or more position joints. The master manipulator sensors are disposed at the orientation joint and the position joint of the robotic arm 801, for obtaining the joint information (the position or the angle) corresponding to the orientation joint and the position joint. In some embodiments, the pose of the master manipulator 800 may be represented by a collection of the joint information of the joints of the master manipulator (e.g., a one-dimensional matrix composed of these joint information). According to the obtained joint information, the current pose of the handle 802 of the master manipulator 800 relative to the master manipulator base coordinate system {CombX} may be determined. For example, the master manipulator 800 may include 7 joints sequentially distributed from a proximal end to a distal end. The proximal end of the master manipulator 800 may be an end close to the master control trolley (e.g., an end connected to the master control trolley), and the distal end of the master manipulator 800 may be an end away from the master control trolley (e.g., an end disposed with the handle 802). Joints 5, 6 and 7 are orientation joints for adjusting the orientation of the handle 802 of the master manipulator 800. Based on the joint information (such as the angle) obtained by the master manipulator sensor of the orientation joint and the forward kinematics algorithm, the current orientation of the master manipulator 800 is calculated. Joints 1, 2 and 3 are position joints for adjusting the position of the handle 802 of the master manipulator 800. Based on the joint information (such as the position) obtained by the master manipulator sensor of the position joint and the forward kinematics algorithm, the current position of the master manipulator 800 is calculated.

Continuing with referring to FIG. 6, at step 603, the target pose of the end of the operating arm may be determined based on the current pose of the master manipulator and the pose relationship between the master manipulator and the end of the operating arm. For example, by establishing a master-slave mapping relationship between the master manipulator and the end of the operating arm, the pose of the end of the operating arm is controlled by remotely operating the master manipulator.

In some embodiments, the pose relationship between the master manipulator and the end of the operating arm may include a relationship between an amount of pose change of the master manipulator and an amount of pose change of the end of the operating arm, such as equal or proportional. In some embodiments, the display coordinate system {Screen} may be consistent with the imaging unit coordinate system {lens} in the definition of the direction of the field of view, so as to obtain an intuitive control experience. There is a predetermined relationship (such as the same or proportional amount of position or orientation change) between the amount of pose change of the imaging unit coordinate system {lens} and the amount of pose change of the master manipulator relative to the reference coordinate system {w}. The imaging unit coordinate system {lens} has a predetermined transformation relationship with the end coordinate system {Tt}, as shown in FIG. 7B, so the amount of pose change of the end coordinate system {Tt} may be calculated based on the amount of pose change of the imaging unit coordinate system {lens}. In this way, the pose relationship may include a relationship between an amount of pose change of the end of the operating arm relative to the current end coordinate system {Tt} and an amount of pose change of the master manipulator relative to the reference coordinate system {w}, such as the same or proportional amount of position or orientation change. The reference coordinate system {w} includes the coordinate system of the space where the master manipulator or operating arm is located, or the world coordinate system. In some embodiments, the step 603 may be performed by the control device 500 (e.g., the pose determination module 520).

Determining the target pose of the end of the operating arm includes: determining a previous pose of the master manipulator, determining a starting pose of the end of the operating arm, and determining a target position of the end of the operating arm based on the previous pose and the current pose of the master manipulator and the starting pose of the end of the operating arm. The previous pose and the current pose of the master manipulator may be the pose of the handle of the master manipulator relative to the master manipulator base coordinate system {CombX} or the reference coordinate system {w}. Based on the previous pose and the current pose of the master manipulator relative to the reference coordinate system {w}, the amount of pose change of the master manipulator relative to the reference coordinate system {w} may be calculated, so as to obtain the amount of pose change of the end of the operating arm relative to the current end coordinate system {Tt}. The starting pose and target pose of the end of the operating arm may be the pose of the end of the operating arm relative to the operating arm base coordinate system {Tb}. The target pose of the end of the operating arm relative to the operating arm base coordinate system {Tb} may be determined based on the starting pose of the end of the operating arm relative to the operating arm base coordinate system {Tb}, the amount of pose change of the end of the operating arm relative to the current end coordinate system {Tt}, and the transformation relationship between the current end coordinate system {Tt} of the operating arm and the operating arm base coordinate system {Tb}. The transformation relationship between the current end coordinate system {Tt} of the operating arm and the operating arm base coordinate system {Tb} may be determined based on the starting pose of the end of the operating arm relative to the operating arm base coordinate system {Tb}.

The pose of the end of the operating arm may include the pose of the end coordinate system {Tt} of the operating arm relative to the operating arm base coordinate system {Tb}. The operating arm base coordinate system {Tb} may be the coordinate system of a base on which the operating arm is mounted, the coordinate system of a sheath sleeve through which the end of the operating arm passes (for example, the coordinate system of an exit of the sheath sleeve), the coordinate system of a Remote Center of Motion (RCM) of the operating arm, etc. For example, the operating arm base coordinate system {Tb} may be disposed at the exit position of the sheath sleeve, and the operating arm base coordinate system {Tb} may remain unchanged during the remote operation.

In some embodiments, previous joint information of at least one joint of the master manipulator may be received, and based on the previous joint information of the at least one joint, the previous pose of the master manipulator is determined. For example, based on the master manipulator sensor reading the joint information of the master manipulator at a previous time and a current time, and the previous pose and the current pose of the handle of the master manipulator are determined. Based on a previous position and a current position of the handle relative to the master manipulator base coordinate system {CombX}, the amount of position change of the handle of the master manipulator is determined. Based on a previous orientation and a current orientation of the handle relative to the master manipulator base coordinate system {CombX}, the amount of orientation change of the handle of the master manipulator is determined.

In some embodiments, a plurality of control cycles may be performed, in each control cycle, a current pose of the master manipulator obtained in a previous round of control cycle is determined as a previous pose of the master manipulator in the current round of control cycle, and a target pose of the end of the operating arm obtained in the previous round of control cycle is determined as a starting pose of the end of the operating arm in the current round of control cycle. For example, for a first round of control cycle, an initial pose of the master manipulator (e.g., a zero position of the master manipulator) may be used as the previous pose of the master manipulator in the first round of control cycle. Similarly, the initial position of the end of the operating arm (e.g., the zero position of the operating arm) may be used as the starting pose of the end of the operating arm in the first round of control cycle. In some embodiments, one control cycle may correspond to a time interval between two frames of images acquired by the imaging unit of the endoscope.

In some embodiments, the amount of pose change of the master manipulator may be determined based on the previous pose and the current pose of the master manipulator. The amount of pose change of the end of the operating arm may be determined based on the amount of pose change of the master manipulator and the pose relationship between the master manipulator and the end of the operating arm. The target pose of the end of the operating arm may be determined based on the starting pose of the end of the operating arm and the amount of pose change of the end of the operating arm.

The pose relationship may include a position relationship and an orientation relationship. The position relationship between the master manipulator and the end of the operating arm may include a relationship between an amount of position change of the master manipulator and an amount of position change of the end of the operating arm, such as equal or proportional. The orientation relationship between the master manipulator and the end of the operating arm may include a relationship between an amount of orientation change of the master manipulator and an amount of orientation change of the end of the operating arm, such as equal or proportional.

In some embodiments, the method 600 further comprises: determining the current position of the handle of the master manipulator relative to the reference coordinate system, determining the previous position of the handle relative to the reference coordinate system, determining the starting position of the end of the operating arm relative to the operating arm base coordinate system, and determining the target position of the end of the operating arm relative to the operating arm base coordinate system based on the previous position and the current position of the handle relative to the reference coordinate system, the transformation relationship between the current end coordinate system of the operating arm and the operating arm base coordinate system, and the starting position of the end of the operating arm relative to the operating arm base coordinate system. The transformation relationship between the current end coordinate system {Tt} of the operating arm and the operating arm base coordinate system {Tb} may be determined based on the starting pose of the end of the operating arm relative to the operating arm base coordinate system {Tb}. For example, in one control cycle, the previous position of the master manipulator in the current round of control cycle may be determined based on the current pose of the master manipulator obtained in the previous round of control cycle, or the previous position of the master manipulator may be determined based on the joint information corresponding to the master manipulator at the previous time read by the master manipulator sensor, and the current position of the master manipulator may be determined based on the joint information corresponding to the master manipulator at the current time read by the master manipulator sensor. The amount of position change of the master manipulator is determined based on the previous position and the current position of the handle relative to the reference coordinate system. The starting position of the end of the operating arm in the current round of control cycle may be determined based on the target pose of the end of the operating arm obtained in the previous round of control cycle. The amount of position change of the end of the operating arm is determined based on the amount of position change of the master manipulator and the pose relationship between the master manipulator and the end of the operating arm. The target position of the end of the operating arm is determined based on the starting position of the end of the operating arm and the amount of position change of the end of the operating arm.

In some embodiments, the method 600 further comprises: determining the current orientation of the handle of the master manipulator relative to the reference coordinate system, determining the previous orientation of the handle relative to the reference coordinate system, determining the starting orientation of the end of the operating arm relative to the operating arm base coordinate system, and determining the target orientation of the end of the operating arm relative to the operating arm base coordinate system based on the previous orientation and the current orientation of the handle relative to the reference coordinate system, the transformation relationship between the current end coordinate system of the operating arm and the operating arm base coordinate system, and the starting orientation of the end of the operating arm relative to the operating arm base coordinate system. The transformation relationship between the current end coordinate system {Tt} of the operating arm and the operating arm base coordinate system {Tb} may be determined based on the starting pose of the end of the operating arm relative to the operating arm base coordinate system {Tb}. For example, in one control cycle, the previous orientation of the master manipulator in the current round of control cycle may be determined based on the current pose of the master manipulator obtained in the previous round of control cycle, or the previous orientation of the master manipulator may be determined based on the joint information corresponding to the master manipulator at the previous time read by the master manipulator sensor, and the current orientation of the master manipulator may be determined based on the joint information corresponding to the master manipulator at the current time read by the master manipulator sensor. The amount of orientation change of the master manipulator is determined based on the previous orientation and the current orientation of the handle relative to the reference coordinate system. The starting orientation of the end of the operating arm in the current round of control cycle may be determined based on the target pose of the end of the operating arm obtained in the previous round of control cycle. The amount of orientation change of the end of the operating arm is determined based on the amount of orientation change of the master manipulator and the pose relationship between the master manipulator and the end of the operating arm. The target orientation of the end of the operating arm is determined based on the starting orientation of the end of the operating arm and the amount of orientation change of the end of the operating arm.

In some embodiments, the main body of the endoscope is provided with an imaging unit, the imaging unit coordinate system {lens} and the end coordinate system {Tt} of the operating arm have a predetermined transformation relationship, and the display coordinate system {Screen} is consistent with the imaging unit coordinate system {lens} in the definition of the direction of the field of view. For example, as shown in FIG. 2, the endoscope 200 includes an endoscope main body 221 and an operating arm 210, an imaging unit is provided on the endoscope main body 221, the imaging unit includes a first imaging unit 230 and a second imaging unit 240, and the first imaging unit coordinate system {lens} or the second imaging unit coordinate system {lens2} has a predetermined transformation relationship with the end coordinate system {Tt} of the operating arm, respectively. The control device (e.g., the control device 500) may generate a composite scene image and/or an actual scene image of an environment around the endoscope under the first image coordinate system {img1} or the second image coordinate system {img2} based on the first image from the first imaging unit and the second image from the second imaging unit, wherein the first image coordinate system {img1} has a predetermined transformation relationship with the first imaging unit coordinate system {lens1}, and the second image coordinate system {img2} has a predetermined transformation relationship with the second imaging unit coordinate system {lens2}. The detailed contents will be described later. The display coordinate system {Screen} may coincide with the first imaging unit coordinate system {lens1} or the second imaging unit coordinate system {lens2} to keep the direction of field of view consistent. The pose change of the image in the display relative to the display coordinate system {Screen} and the pose change of the end of the operating arm relative to the operating arm base coordinate system {Tb} are kept to be consistent in the amount of pose change and opposite in a change direction. In this way, when the operator holds the handle of the master manipulator to operate, the pose change of the image in the display felt by the operator and the pose change of the handle of the master manipulator perceived by the operator maintain a preset transformation relationship.

In some embodiments, when the display displays images from different imaging units, transformation relationships between different imaging unit coordinate systems and the operating arm end coordinate system may be used. For example, when the display displays the first image from the first imaging unit, a predetermined transformation relationship between the first imaging unit coordinate system {lens1} and the end coordinate system {Tt} of the operating arm may be used in the control.

Continuing with reference to FIG. 6, at step 605, a drive instruction for driving the end of the operating arm may be generated based on the target pose. For example, the drive signal for the operating arm may be calculated based on the target pose of the end of the operating arm relative to the operating arm base coordinate system {Tb}. In some embodiments, the control device may, based on the target pose of the end of the operating arm, send the drive signal to at least one drive device to control the motion of the end of the operating arm. In some embodiments, the control device may determine the drive signal for the at least one drive device controlling the motion of the operating arm based on the target pose of the end of the operating arm by an inverse kinematics numerical iteration algorithm of kinematic model of an operating arm. It should be understood that the kinematic model may represent a mathematical model of a kinematic relationship between a joint space and a task space of the operating arm. For example, the kinematic model may be established by methods such as DH (Denavit-Hartenberg) parametric method and exponential product notation. In some embodiments, the target pose of the end of the operating arm is the target pose of the end of the operating arm in the reference coordinate system. In some embodiments, the step 605 may be performed by the control device 500 (e.g., the drive module 520).

Continuing with reference to FIG. 6, at step 607, a first image is obtained from the first imaging unit. In some embodiments, the first imaging unit is configured to be located on one side of the main body of the endoscope with respect to the end instrument. During the movement of the endoscope within the scene, the first imaging unit continuously takes the first images in a first field of view, and the control device 500 (e.g., an image processing module 530) may receive the first images from the first imaging unit. In some embodiments, the end instrument is located in the first field of view of the first imaging unit, and the first image comprises an image of the end instrument taken from the one side of the main body.

Continuing with reference to FIG. 6, at step 609, a second image is obtained from the second imaging unit, wherein the first image and the second image have different fields of view and include images of the end instrument. In some embodiments, the second imaging unit is configured to be located on the other side of the main body of the endoscope with respect to the end instrument. During the movement of the endoscope within the scene, the second imaging unit continuously takes the second images in a second field of view different from the first field of view of the first imaging unit, and the control device 500 (e.g., the image processing module 530) may receive the second images from the second imaging unit. In some embodiments, the end instrument is located in the second field of view of the second imaging unit, and the second image comprises an image of the end instrument taken from the other side of the main body.

Continuing with reference to FIG. 6, at step 611, based on the first image and the second image, a composite scene image is generated to remove an actual image of the end instrument. In the present disclosure, due to the occlusion of the end instrument, the first imaging unit and the second imaging unit each cannot photograph the entire scene. In some embodiments, the control device 500 (e.g., the image processing module 530) may use one of the first image or the second image to fill a portion of the other image that is blocked by the end instrument through a computer vision processing, thereby generating a two-dimensional composite scene image or a three-dimensional composite scene image with the end instrument being removed. For example, an exemplary method of generating the composite scene image based on the first image and the second image may include a method 1200 as shown in FIG. 12. In some embodiments, the computer vision processing may include a feature point detection algorithm, which may extract feature points in the first image and the second image for matching, thereby enabling a two-dimensional stitching of the first image and the second image. In some embodiments, the computer vision processing may include an image sequence optical flow reconstruction algorithm, which may determine a depth of a pixel in the scene space based on an optical flow of the pixel in the image, thereby enabling a three-dimensional reconstruction of the scene. By generating the composite scene image, a more complete image for the scene, which is at least partially unblocked by the end instrument, can be displayed on the display device, thereby facilitating the operator to observe a lumen and an operating area without hindrance.

Figure 17:
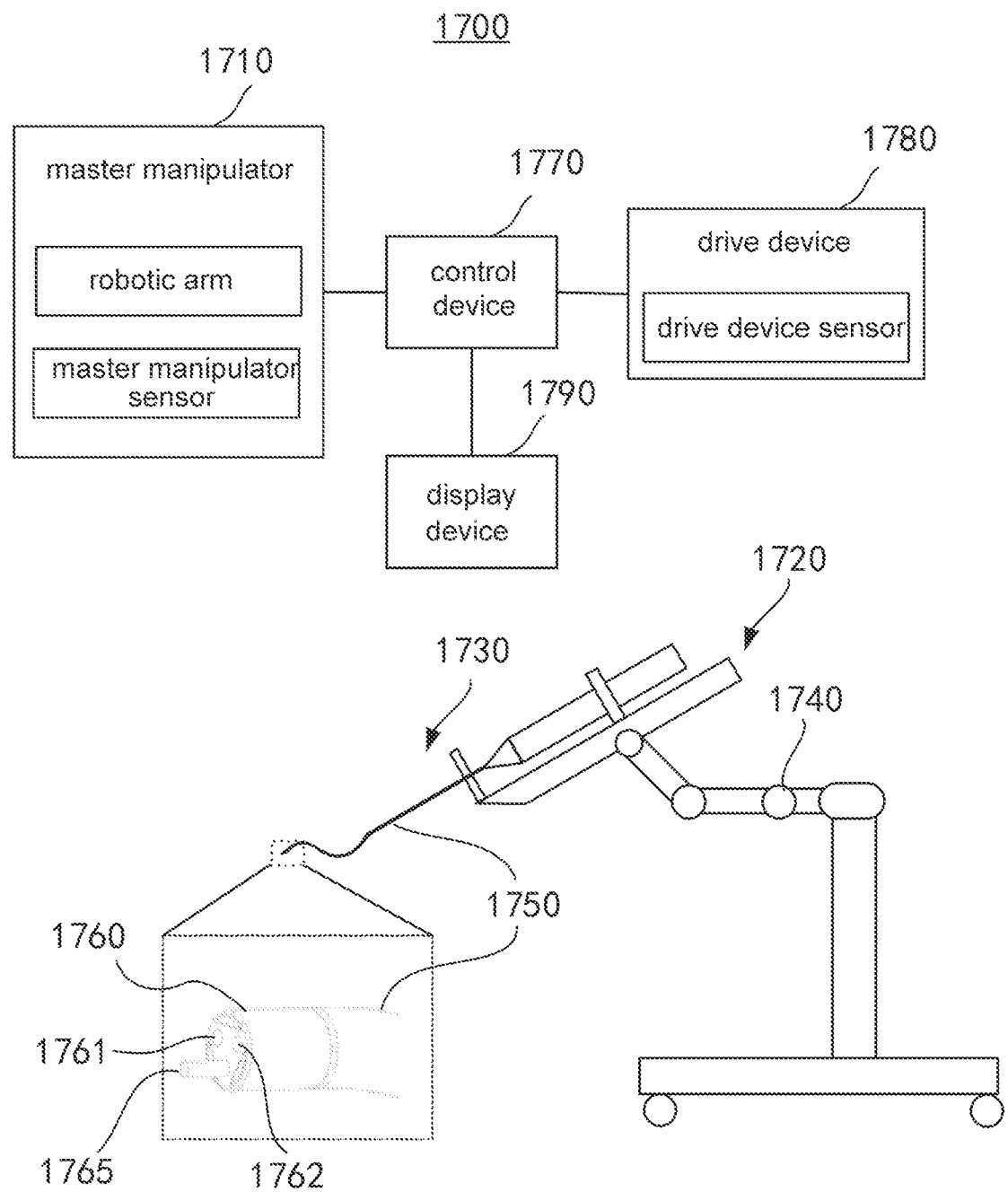
FIG. 17 shows a schematic diagram of a robot system according to some embodiments of the present disclosure.

Continuing with reference to FIG. 6, at step 613, a virtual image of the end instrument is generated in the composite scene image. For example, an exemplary method of generating the virtual image of the end instrument in the composite scene image may include a method 1700 as shown in FIG. 17. In some embodiments, the control device 500 (e.g., a virtual image generation module 540) may generate the virtual image of the end instrument at a position corresponding to the end instrument in the composite scene image by a real-time rendering method. By generating the virtual image of the end instrument in the composite scene image, the operator can be reminded with an actual position and size of the end instrument without hindering the operator from observing the scene, so as to avoid colliding with a wall surface of the lumen or the operating area due to the inability to see the end instrument during operation.

In some embodiments, the method 600 may further include scene mode switching based on a display mode instruction. FIG. 9 shows a flowchart of a method 900 of displaying a scene image based on a display mode instruction according to some embodiments of the present disclosure. In some embodiments, part or all of the steps in the method 900 may be performed by the control device (e.g., the control device 500 shown in FIG. 5 or the control device 1770 shown in FIG. 17) of the robot system (e.g., the robot system 100 shown in FIG. 1 or the robot system 1700 shown in FIG. 17). The control device may include a computing device. The method 900 may be implemented by software, firmware and/or hardware. In some embodiments, the method 900 may be implemented as computer-readable instructions. These instructions may be read and executed by a general-purpose processor or a dedicated processor (e.g., the control device 1770 shown in FIG. 17). In some embodiments, these instructions may be stored on a computer-readable medium.

Figure 16:
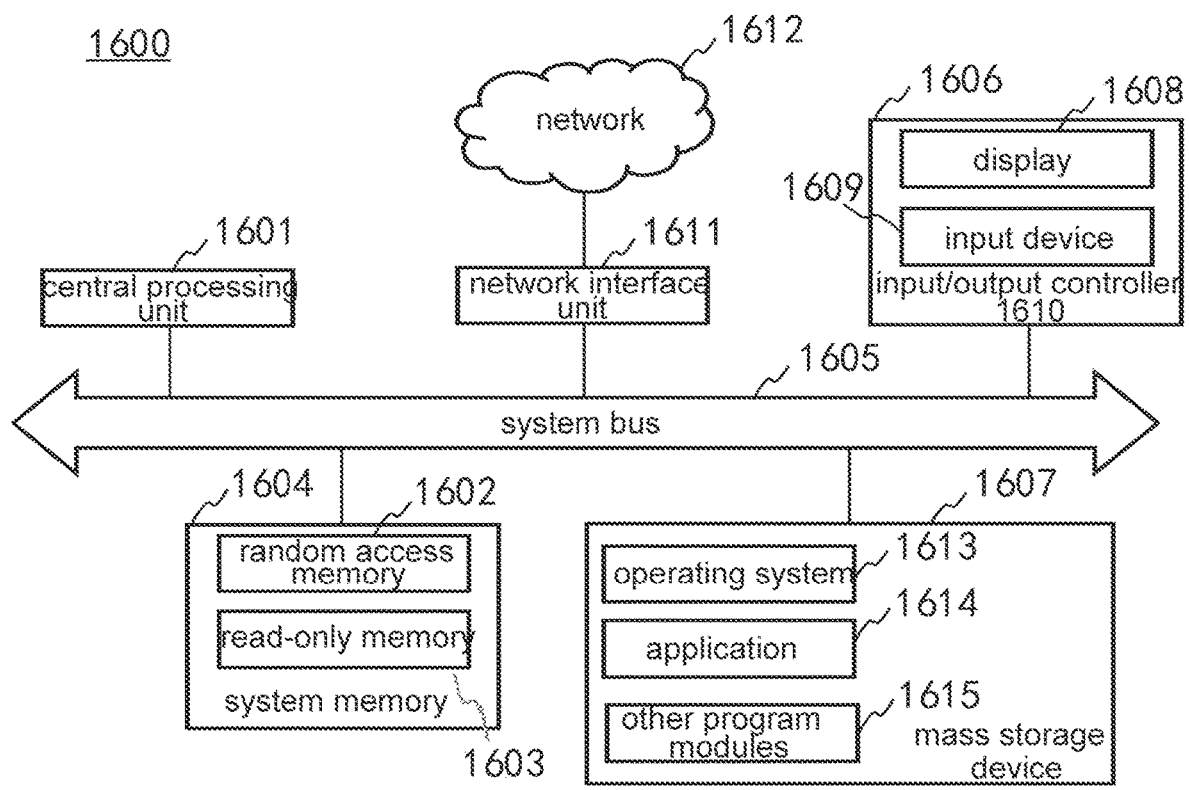
FIG. 16 shows a schematic block diagram of a computer device according to some embodiments of the present disclosure.

With reference to FIG. 9, at step 901, an actual scene image is generated based on the first image and/or the second image to display an actual image of the end instrument. In some embodiments, the first image taken by the first imaging unit or the second image taken by the second imaging unit may be used as a two-dimensional actual scene image, which comprises the actual image of the end instrument. In some embodiments, the control device 500 (e.g., the image processing module 530) may generate a three-dimensional actual scene image by a computer vision algorithm based on the first image or the second image. For example, an exemplary method of generating the three-dimensional actual scene image based on the first image or the second image may include a method 1600 as shown in FIG. 16. In some embodiments, the computer vision algorithm may include an image sequence optical flow reconstruction algorithm, which may determine a depth of a pixel in the scene space based on an optical flow of the pixel in the first image or the second image, thereby enabling a three-dimensional reconstruction of the actual scene. In some embodiments, two actual scene images with different fields of view may also be generated simultaneously based on the first image and the second image, for being displayed side by side on the display device.

Continuing with reference to FIG. 9, at step 903, the composite scene image with the virtual image of the end instrument and/or the actual scene image is displayed in response to the display mode instruction. The display mode instruction may include, for example, at least one of a drive instruction, an end instrument operation instruction and a display mode selection instruction.

The drive instruction is used to drive the operating arm to move, to control the endoscope to move within the cavity. In some embodiments, the method 900 further comprises: generating, in response to the drive instruction, a first display signal to display at least the composite scene image with a virtual image. In some embodiments, the drive instruction for driving the operating arm to move may include a feed instruction, a retreat instruction, or a steering instruction of the endoscope. For example, the drive instruction may be determined based on the operation of the operator on the master manipulator, the display signal generation module 550 of the control device 500 may generate a first display signal in response to the drive instruction, the scene output module 560 may in response to the first display signal, output at least a composite scene picture with a virtual image of the end instrument to the display device for display, and the drive module 520 may control the endoscope to feed, withdraw or steer based on the drive instruction. By displaying at least the composite scene image with the end instrument removed, it can be avoided that the operator operates the endoscope to feed or steer in an incomplete field of view, thus undertaking an unnecessary surgical risk. On the other hand, by at least displaying the composite scene image with the end instrument removed when the endoscope is controlled to withdraw from the operating area and the lumen, it can facilitate the operator to observe a surgical effect or control the endoscope to exit safely. In some embodiments, based on the master-slave motion mapping relationship between the pose of the master manipulator and the pose of the end of the operating arm and the current pose of the master manipulator, the target pose of the end of the operating arm of the endoscope may be determined, and then based on the target pose of the end of the operating arm, the drive instruction may be generated. The drive instruction may be, for example, a drive signal related to the target pose. In some embodiments, the method of determining the target pose of the end of the operating arm may be implemented similarly to step 603 in the method 600, and the method of generating the drive instruction may be implemented similarly to step 605 in the method 600.

The end instrument operation instruction may be used to control an operation of the end instrument. In some embodiments, the method 900 may further include generating, in response to the end instrument operation instruction, a second display signal to at least display an actual scene image. In some embodiments, the end instrument operation instruction may include an activation instruction for the end instrument, and the activation instruction is used to instruct to start the operation of end instrument. In the case where the end instrument is an electrocoagulation hemostatic device, the activation instruction may be, for example, to turn on a power supply. In some embodiments, the scene output module 560 of the control device 500 may in response to the end instrument operation instruction, display the actual scene image or switch the displayed picture from the composite scene image with the virtual image of the end instrument to the actual scene image, thereby allowing the operator to perform surgical tasks in the case of observing the end instrument, facilitating to improve accuracy of the operation. In some embodiments, in response to the operator completing or temporarily aborting the operation of the end instrument, such as turning off the power supply, the scene output module 560 of the control device 500 may display the composite scene image with the virtual image of the end instrument or switch the displayed picture from the actual scene image to the composite scene image with the virtual image of the end instrument, thereby allowing the operator to confirm the effect of the surgical tasks in a full field of view. In some embodiments, the end instrument operation instruction may has higher priority in display mode control than other drive instructions other than the retreat instruction and an automatic exit instruction (as described below). In this way, when the end instrument is triggered to start operating, the operator can more intuitively see an actual situation in the body.

Those skilled in the art will appreciate that, in the present disclosure, the display mode control priority refers that in the case of a plurality of display mode instructions existing simultaneously, a display mode instruction with a higher priority has a higher control priority. In some embodiments, the operator may at the same time of issuing the end instrument operation instruction, control the endoscope to feed or steer by the feed instruction or the steering instruction, to achieve a first composite operation of controlling the motion of the endoscope when activating the end instrument for operation. For example, in the case that the end instrument is the electrocoagulation hemostatic device, the operator may control the endoscope to feed while activating the electrocoagulation hemostatic device, so as to achieve the slight contact and press of the electrocoagulation hemostatic device on the tissue. By displaying the actual scene images preferentially based on the end instrument operation instruction, it can be ensured that the operator performs surgical tasks based on the actual situation in the body. Similarly, for other composite operations containing a variety of operations, the display modes may also be controlled based on the display mode control priority of various operations or operation instructions.

In some embodiments, the method 900 may further include based on the retreat instruction in the drive instruction, controlling the endoscope to move away from the operating area; and generating, in response to a distance of the endoscope away from the operating area exceeding a threshold, the first display signal to display at least the composite scene image with the virtual image. The distance of the endoscope away from the operating area exceeding the threshold may include determining whether a distance for which the endoscope retreats exceeds the threshold, or determining whether a cumulative value of an amount of position change of the master manipulator that corresponds to the retreat instruction exceeds the threshold, wherein the amount of position change corresponds to the retreat instruction in the drive instruction. For example, as shown in FIG. 7A, the amount of position change of the master manipulator that corresponds to the retreat instruction may be an amount of position change of the master manipulator handle coordinate system (H) in a negative direction of $\hat{z}_w$ of the reference coordinate system $\{w\}$ (e.g., a world coordinate system). For example, in a plurality of control cycles, the retreat instruction proportional to the amount of position change of the master manipulator may be determined based on the operation of the operator on the master manipulator. The drive module 520 of the control device 500 may control the endoscope to move away from the operating area based on the retreat instruction, and the control device 500 may obtain an amount of retreat position change of the master manipulator in each control cycle (e.g., stored to a memory), and accumulate these amounts of position change. When a accumulated value of the amounts of position change exceeds a predetermined threshold, the display signal generation module 550 sends a first display signal to the scene output module 560 to display at least the composite scene image with the virtual image, so as to facilitate the operator to observe and avoid injury to internal organs or lumens during the retreating. In the priority of display mode control, this display operation for the retreat instruction may has higher priority than other drive instructions (such as the feed instruction or the steering instruction, etc.) other than an automatic exit instruction (as described below) and the end instrument operation instruction. In this way, when the operator has an intention to withdraw the endoscope, the display mode can be automatically adjusted in time, facilitating the operator to observe the situation in the body. In some embodiments, the operator may at the same time of issuing the end instrument operation instruction, control the endoscope to withdraw by the retreat instruction, to achieve a second composite operation of controlling the motion of the endoscope when activating the end instrument for operation. For example, in the case where the end instrument is the clamp-type device, the operator may at the same time of activating the clamp-type device to clamp a tissue, control the endoscope to retreat, to achieve a slight traction and peeling of the clamp-type device to the tissue. By displaying the actual scene image based on the end instrument operation instruction when the distance of the endoscope away from the operating area is below a threshold, and displaying the composite scene image with the virtual image of the end instrument preferentially based on the retreat instruction when the distance of the endoscope away from the operating area exceeds the threshold, an actual or full field of view in the body can be automatically provided to the operator for easy observation. In some embodiments, the method 1100 may further comprise terminating, in response to the distance of the endoscope away from the operating area exceeding the threshold, the end instrument operation instruction. In this way, the end instrument can be prevented from injuring the internal organs or lumens during a retreat process of the endoscope.

In some embodiments, the drive instruction for controlling the motion of the endoscope may further include an automatic exit instruction which may be used to control the endoscope to automatically exit from the human body. In some embodiments, the method 900 may further include controlling the endoscope to exit from the human body based on the automatic exit instruction, and generating, in response to the automatic exit instruction, a first display signal to display at least the composite scene image with the virtual image. The automatic exit instruction may allow the operator to withdraw the endoscope quickly. Similarly, the automatic exit instruction may have higher priority in display mode control than other drive instructions (e.g., the feed instruction, the steering instruction, or the retreat instruction etc.) and the end instrument operation instruction. In addition, the automatic exit instruction may automatically terminate other drive instructions and the end instrument operation instruction that are being executed, and may disable other drive instructions, the end instrument operation instruction or a display mode selection instruction. Alternatively, the automatic exit instruction can also allow the display mode selection instruction to be triggered during execution, so as to facilitate the operator to switch the display mode and better observe the situation in the body.

The display mode selection instruction can be used to manually trigger the switch of the display mode, for example, through a manual input by the operator. In some embodiments, the display mode selection instruction may include at least one of a composite scene display instruction, an actual scene display instruction and a multi-scene display instruction. Among them, the composite scene display instruction is used to display the composite scene image with the virtual image of the end instrument, the actual scene display instruction is used to display the actual scene image, and the multi-scene display instruction is used to display the composite scene image with the virtual image of the end instrument and the actual scene image simultaneously. For example, the multi-scene display instruction may be used to display at least a portion of the actual scene image in a first window of the display device, and display at least a portion of the composite scene image with the virtual image of the end instrument in a second window of the display device.

In some embodiments, the display mode selection instruction may has higher priority in display mode control than other display mode instructions (such as the drive instruction and the end instrument operation instruction, etc.). Since the display mode selection instruction needs to be triggered by the operator, expressing a direct display demand of the operator, it may have a high priority in the operation.

FIG. 10 shows a schematic diagram of a multi-scene display on a display device 1000 according to some embodiments of the present disclosure. As shown in FIG. 10, in some embodiments, the display device 1000 may include a first window 1010 and a second window 1020, and the first window 1010 encloses the second window 1020 from the outside, forming a so-called picture-in-picture display mode. In some embodiments, at least a portion of the actual scene image may be displayed in the first window 1010, and at least a portion of the composite scene image with the virtual image of the end instrument may be displayed in the second window 1020. For example, the scene output module 950 of the control device 900 may in response to the multi-scene display instruction, simultaneously output the actual scene image and the composite scene image with the virtual image of the end instrument to the display device 1000. The display device 1000 may display a portion of the actual scene image in the first window 1010, and display for example, a surgical site in the composite scene image with the virtual image of the end instrument in the second window 1020. Such way of displaying allows the operator to see both the environment around the endoscope and the surgical site located in front of the end instrument simultaneously, which can improve the accuracy of the operation while suppressing a discomfort of the operator caused by repeated image switching. It should be understood that the way of presenting two scene images simultaneously on the display device includes, but is not limited to, the above described way. For example, the display device 1000 may also display the first window 1010 and the second window 1020 side by side in a form of left and right split screens.

Some embodiments of the present disclosure provide a method of generating a composite scene image based on a first image and a second image. FIG. 11 shows a flowchart of a method 1100 of generating a composite scene image based on a first image and a second image according to some embodiments of the present disclosure. In some embodiments, part or all of the steps in the method 1100 may be performed by the control device (e.g., the control device 500 shown in FIG. 5 or the control device 1770 shown in FIG. 17) of the robot system (e.g., the robot system 100 shown in FIG. 1 or the robot system 1700 shown in FIG. 17). The control device may include a computing device. The method 1100 may be implemented by software, firmware and/or hardware. In some embodiments, the method 1100 may be implemented as computer-readable instructions. These instructions may be read and executed by a general-purpose processor or a dedicated processor (e.g., the control device 1770 shown in FIG. 17). In some embodiments, these instructions may be stored on a computer-readable medium.

Referring to FIG. 11, at step 1101, a supplementary image is determined based on the first image or the second image. The supplementary image includes a portion of the second image or the first image that is blocked by the end instrument. In some embodiments, the supplementary image may be determined based on the first image, and the supplementary image comprises a portion of the second image that is blocked by the end instrument. For example, as shown in FIG. 4, the first imaging unit 430 may take the first image in the first field of view (e.g., a sum of the field of view 431 and the field of view 432). The first image includes a first environment image (e.g., an image of a lumen wall surface) within the field of view 431 and an image of the end instrument 460 located within the field of view 432. The first environment image may include an image within a field of view 431' (a part of the field of view 431), and the image is a supplementary image for synthesis with the second image taken by the second imaging unit 440, and corresponds to the portion of the second image that is blocked by the end instrument 460. Similarly, in some embodiments, the supplementary image may be determined based on the second image, and the supplementary image comprises a portion of the first image that is blocked by the end instrument. For example, the second imaging unit 440 may take the second image in the second field of view (e.g., a sum of the field of view 441 and the field of view 442). The second image includes a second environment image (e.g., an image of a lumen wall surface) within the field of view 441 and an image of the end instrument 460 located within the field of view 442. The second environment image may include an image within a field of view 441' (a part of the field of view 441), and the image is a supplementary image for synthesis with the first image taken by the first imaging unit 430, and corresponds to the portion of the first image that is blocked by the end instrument 460.

In some embodiments, a position of the supplementary image in the first image or a position of the supplementary image in the second image may be determined based on a spatial positional relationship between the first imaging unit 430, the second imaging unit 440 and the end instrument 460, thereby separating the supplementary image from the first image or the second image. The supplementary image may be used to stitch with the second environment image in the second image or the first environment image in the first image to generate a stitched image.

Continuing with reference to FIG. 11, at step 1103, the first environment image or the second environment image are determined based on the first image or the second image. The first environment image and the second environment image do not include the image of the end instrument. In some embodiments, the image of the end instrument 460 may be removed from the first image or the second image based on a difference between the environment image and the image of the end instrument 460, obtaining the first environment image in the first image or the second environment image in the second image. For example, the image of the end instrument 460 may be removed from the first image or the second image based on color features, boundary features, texture features or spatial relationship features, to generate the first environment image or the second environment image.

Continuing with reference to FIG. 1, at step 1105, the first environment image or the second environment image and the supplementary image are stitched to generate the stitched image. Stitching the first environment image and the supplementary image to generate the stitched image is described as an example below, but it should be understood that it is also possible to generate the stitched image by stitching the second environment image and the supplementary image.

In some embodiments, a feature point detection algorithm may be used to extract feature points from the first environment image and the supplementary image respectively. The feature point detection algorithm may be any one of a Harris (corner detection) algorithm, a SIFT (Scale Invariant Feature Transform) algorithm, a SURF (Speeded-Up Robust Features) algorithm or an ORB (Oriented Fast and Rotated Brief, feature descriptor) algorithm. For example, the feature point detection algorithm can extract the feature points from the edges of the first environment image and the supplementary image respectively, and establish a feature point database of the image according to a data structure of the feature points. The data structure of the feature points may include a location coordinate, a scale, a direction and a feature vector of the feature points.

In some embodiments, a feature matching algorithm may be used to perform a feature matching on the feature points of the edges of the first environment image and the supplementary image, thereby determining a correlation between the edge of the first environment image and the edge of the supplementary image. The feature matching algorithm may be any one of a brute force matching algorithm, a cross-matching algorithm, a KNN (k-nearest neighbor classification) matching algorithms, a RANSAC (Random Sample Consensus) matching algorithm.

In some embodiments, a registration image may be generated based on the first environment image and/or the supplementary image. For example, a transformation relationship between the first image coordinate system {img1} and the second image coordinate system {img2} may be determined based on a spatial positional relationship between the first imaging unit 430 and the second imaging unit 440 (e.g., a transformation relationship between the first imaging unit coordinate system {lens1} and the second imaging unit coordinate system {lens2}), and based on this transformation relationship, the supplementary image under the second image coordinate system {img2} is converted into an image under the first image coordinate system {img1}, generating a registration image for image fusion with the first environment image. In some embodiments, it may also be possible to convert the first environment image and the supplementary image into images under the reference coordinate system {w} based on transformation relationships among the first image coordinate system {img1}, the second image coordinate system {img2} and a reference coordinate system {w} (e.g., a coordinate system of the end of the main body of the endoscope).

In some embodiments, the stitched image may be generated by stitching the first environment image and the registration image. For example, the edges of the first environment image and the registration image may be aligned and stitched based on successful matched feature points in the first environment image and the supplementary image, thereby generating the stitched image. In some embodiments, the resulting stitched image may be a two-dimensional stitched image. In some embodiments, the two-dimensional stitched image may be used as a two-dimensional composite scene image.

In some embodiments, the method 1100 may further include further processing the first environment image, the second environment image, the supplementary image or the stitched image to generate a three-dimensional composite scene image. FIG. 12 shows a flowchart of a method 1200 of generating a three-dimensional composite scene image based on a first image and a second image according to some embodiments of the present disclosure. In some embodiments, part or all of the steps in the method 1200 may be performed by the control device (e.g., the control device 500 shown in FIG. 5 or the control device 1770 shown in FIG. 17) of the robot system (e.g., the robot system 100 shown in FIG. 1 or the robot system 1700 shown in FIG. 17). The control device may include a computing device. The method 1200 may be implemented by software, firmware and/or hardware. In some embodiments, the method 1200 may be implemented as computer-readable instructions. These instructions may be read and executed by a general-purpose processor or a dedicated processor (e.g., the control device 1770 shown in FIG. 17). In some embodiments, these instructions may be stored on a computer-readable medium.

Referring to FIG. 12, at step 1201, for at least one of the first environment image, the second environment image, the supplementary image or the stitched image, an optical flow field of the image is determined based on the image and a previous frame image of the image (images in two consecutive frames). The optical flow field comprises optical flows of a plurality of pixels in the image. The first environment image in the first image is described as an example below.

In some embodiments, during the movement of the endoscope (e.g., the endoscope 420) within the lumen, the first imaging unit (e.g., the first imaging unit 430) photographs a lumen environment in continuously varying fields of view (corresponding to a direction of an optical axis), to obtain a plurality of first images arranged in accordance with a frame sequence. The first environment image may be determined by removing the image of the end instrument (e.g., the end instrument 460) from the first image. The method of determining the first environment image may be achieved similarly to the step 1103 in the method 1100.

A pixels in the first environment image corresponds to object points in the environment, and in the sequence of the first environment images, the pixel moves between adjacent frames (for example, a previous frame and a current frame of the image) to produce an optical flow, wherein the optical flow is a two-dimensional vector used to describe a position change of the pixel, corresponds to a three-dimensional motion vector of the object point in the environment, and is a projection of the three-dimensional motion vector of the object point on an image plane. In some embodiments, the optical flows of the pixels in the first environment image may be calculated through the previous frame and the current frame of the first environment image. In some embodiments, by calculating the optical flows for a plurality of pixels in the first environment image, an optical flow field of the first environment image may be obtained. The optical flow field is an instantaneous velocity field generated by the movement of the pixels of the first environment image on the image plane, and includes instantaneous motion vector information of the pixel, such as a direction of motion and a speed of motion of the pixel.

Continuing with reference to FIG. 12, at step 1203, a depth map of the image is generated based on the optical flow field of the image and the pose of the imaging unit corresponding to the image. The depth map comprises depths of the object points corresponding to the plurality of pixels. In some embodiments, based on the optical flow of the pixel in the optical flow field of the first environment image and a pose change of the first imaging unit, a depth value of the object point in the lumen environment corresponding to the pixel may be determined, thereby generating the depth map of the first environment image based on the depth of the object point. For example, an exemplary method of generating the depth map of the image based on the optical flow field and the pose of the imaging unit may include a method 1300 as shown in FIG. 13.

Figure 13:
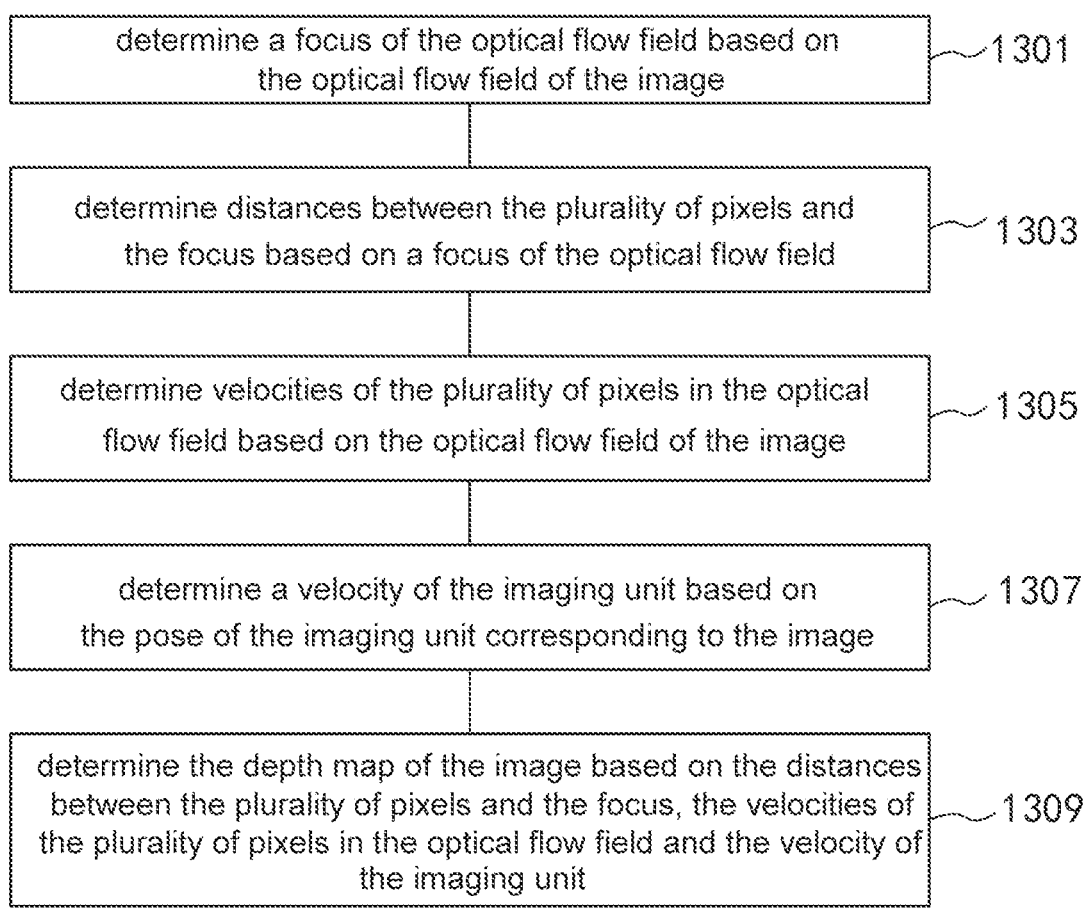
FIG. 13 shows a flowchart of a method of generating a depth map based on an optical flow field and a pose of the imaging unit according to some embodiments of the present disclosure.

FIG. 13 shows a flowchart of a method 1300 of generating a depth map based on an optical flow field and a pose of an imaging unit according to some embodiments of the present disclosure. In some embodiments, part or all of the steps in the method 1300 may be performed by the control device (e.g., the control device 500 shown in FIG. 5 or the control device 1770 shown in FIG. 17) of the robot system (e.g., the robot system 100 shown in FIG. 1 or the robot system 1700 shown in FIG. 17). The control device may include a computing device. The method 1300 may be implemented by software, firmware and/or hardware. In some embodiments, the method 1300 may be implemented as computer-readable instructions. These instructions may be read and executed by a general-purpose processor or a dedicated processor (e.g., the control device 1770 shown in FIG. 17). In some embodiments, these instructions may be stored on a computer-readable medium.

Referring to FIG. 13, at step 1301, a focus of the optical flow field is determined based on the optical flow field of the image. For example, when generating the optical flow field based on the first environment image, in the case where the endoscope feeds or retreats, the optical flows of a plurality of pixels in the first environment image are not parallel to each other, and an extension line of an optical flow vector converges on the focus of the optical flow field, which is a fixed point in the optical flow field. In some embodiments, the optical flow vector in the optical flow field may have a correspondence with the focus, and each optical flow vector may separately converge to a different focus. In some embodiments, for example, when the endoscope feeds, the focus of the optical flow field may include a Focus of expansion (FOE), and the POE is a convergence point of the reverse extension of the optical flow vectors. In some embodiments, for example, when the endoscope retreats, the focus of the optical flow field may include a Focus of contraction (FOC), and the FOC is a convergence point of the forward extension of the optical flow vectors.

Continuing with reference to FIG. 13, at step 1303, distances between the plurality of pixels and the focus are determined based on the focus of the optical flow field. For example, in the first environment image, the distance between each of the plurality of pixels and the focus may be determined in the first image coordinate system.

Continuing with reference to FIG. 13, at step 1305, velocities of the plurality of pixels in the optical flow field are determined based on the optical flow field of the image. The velocity of the optical flow of the pixel may be a ratio of a distance (a length of the optical flow) for which the pixel moves in the optical flow field to a time interval of two consecutive frames. In some embodiments, in the first environment image, the distance for which each of the plurality of pixels moves in the optical flow field may be determined in the first image coordinate system. In some embodiments, the time interval between two consecutive frames (time per frame) may be, for example, 1/60 second, but not limited thereto, it may be appropriately adjusted according to imaging requirements.

Continuing with reference to FIG. 13, at step 1307, a velocity of the imaging unit is determined based on the pose of the imaging unit corresponding to the image. In some embodiments, the pose of the imaging unit may be determined based on the target pose of the end of the operating arm and the pose relationship between the end of the operating arm and the imaging unit. For example, the pose of the first imaging unit may be determined based on the target pose of the end of the operating arm and the pose transformation relationship between the first imaging unit coordinate system {lens1} and the end coordinate system {Tt} of the operating arm. In some embodiments, the method of determining the target pose of the end of the operating arm may be implemented similarly to the step 603 in the method 600. In some embodiments, the previous pose and the current pose of the first imaging unit may be determined based on the starting pose and the target pose of the end of the operating arm in one control cycle. The previous pose of the first imaging unit corresponds to the previous frame of the image, and may be obtained based on the starting pose of the end of the operating arm in one control cycle, and the current pose of the first imaging unit corresponds to the current frame of the image, and may be obtained based on the target pose of the end of the operating arm in the same control cycle. Based on the previous pose and the current pose of the first imaging unit, a moving distance of the first imaging unit may be determined, so as to determine a velocity of the first imaging unit based on the moving distance of the first imaging unit and a time interval between two consecutive frames.

Continuing with reference to FIG. 13, at step 1309, the depth map of the image is determined based on the distances between the plurality of pixels and the focus, the velocities of the plurality of pixels in the optical flow field and the velocity of the imaging unit. In some embodiments, in the optical flow field generated from the first environment image, a depth value (depth information) of the object point may be determined based on the distance between one pixel and the focus, the velocity of the pixel in the optical flow field and the velocity of the first imaging unit. The depth value of the object point may be a distance from the object point to the image plane of the first imaging unit. The depth map of the first environment image may be obtained by calculating the depth value of the object point for each pixel in the first environment image.

In some embodiments, it may also be possible to determine the distance for which each of the plurality of pixels moves in the optical flow field based on the optical flow field of the image, and determine the moving distance of the imaging unit based on the pose of the imaging unit corresponding to the image. Thus, the depth map of the image is determined based on the distance between each of the plurality of pixels and the focus, the distance for which each of the plurality of pixels moves in the optical flow field, and the moving distance of the imaging unit.

Continuing with reference to FIG. 12, at step 1205, object point spatial coordinates of the object points corresponding to the plurality of pixels are determined based on the depth map of the image and pixel coordinates of the plurality of pixels. In some embodiments, the object point spatial coordinate of the object point may be determined based on the pixel coordinate of the pixel of the first environment image in the first image coordinate system and the depth value of the object point corresponding to the pixel, thereby realizing the transformation of a two-dimensional pixel in the first environment image to a three-dimensional coordinate.

Continuing with reference to FIG. 12, at step 1207, color information of the plurality of pixels is obtained based on the image. In some embodiments, a color feature extraction algorithm may be used to extract the color information of the pixels in the first environment image. The color feature extraction algorithm may be any one of methods such as a color histogram, a color set, a color moment, a color aggregation vector, and so on.

Continuing with reference to FIG. 12, at step 1209, a point cloud fusion is performed on the image based on the color information of the plurality of pixels and the object point spatial coordinates, to generate a three-dimensional point cloud. In some embodiments, the object point spatial coordinate of the object point may be converted based on an intrinsics matrix of the first imaging unit, and the point cloud fusion is performed on the first environment image based on the color information of the pixels, to generate the three-dimensional point cloud. The three-dimensional point cloud includes three-dimensional spatial coordinates and color information of the object points. In some embodiments, the intrinsics of the first imaging unit may be known or obtained by calibration.

In some embodiments, the method 1200 may be employed to process the first environment image or the second environment image and the supplementary image to generate the three-dimensional point clouds. For example, in some embodiments, a feature extraction and stereo matching may be performed on the three-dimensional point clouds of the first environment image and the supplementary image, to achieve the stitching of the first environment image and the supplementary image, thereby generating a three-dimensional stitched image. In some embodiments, it may also be possible to use the method 1200 to process a registration image generated based on the supplementary image to generate a three-dimensional point cloud, and perform a feature extraction and stereo matching on the three-dimensional point clouds of the first environment image and the registration image, thereby stitching to generate a three-dimensional stitched image. It should be understood that it may also be possible to stitch the second environment image in the second image and a corresponding supplementary image to generate the three-dimensional stitched image.

In some embodiments, the two-dimensional stitched image or the three-dimensional stitched image may be used as the composite scene image. In some embodiments, the two-dimensional composite scene image may also be processed to generate the three-dimensional composite scene image. For example, the method 1200 may be used to process the stitched image generated in the method 1100 to achieve the conversion of the composite scene image from two-dimensional to three-dimensional.

Figure 14:
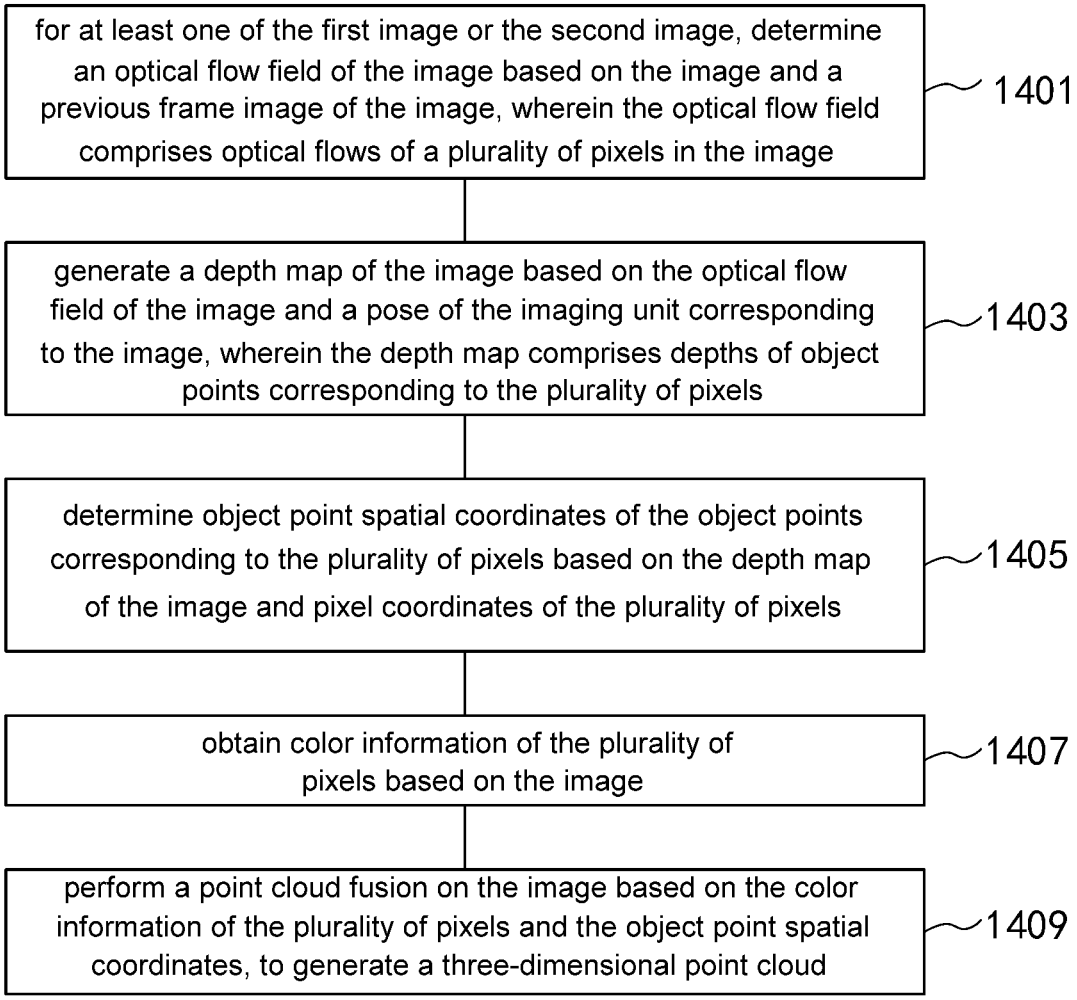
FIG. 14 shows a flowchart of a method of generating a three-dimensional actual scene image based on a first image and/or a second image according to some embodiments of the present disclosure.

In some embodiments, the method 1100 may further include generating a three-dimensional actual scene image based on at least one of the first image or the second image. FIG. 14 shows a flowchart of a method 1400 of generating a three-dimensional actual scene image based on a first image and/or a second image according to some embodiments of the present disclosure. In some embodiments, part or all of the steps in the method 1400 may be performed by the control device (e.g., the control device 500 shown in FIG. 5 or the control device 1770 shown in FIG. 17) of the robot system (e.g., the robot system 100 shown in FIG. 1 or the robot system 1700 shown in FIG. 17). The control device may include a computing device. The method 1400 may be implemented by software, firmware and/or hardware. In some embodiments, the method 1400 may be implemented as computer-readable instructions. These instructions may be read and executed by a general-purpose processor or a dedicated processor (e.g., the control device 1770 shown in FIG. 17). In some embodiments, these instructions may be stored on a computer-readable medium.

Referring to FIG. 14, at step 1401, for the first image or the second image, the optical flow field of the image is determined based on the image and a previous frame image of the image. The optical flow field comprises optical flows of a plurality of pixels in the image. In some embodiments, the step 1401 may be similarly implemented as the step 1201 in the method 1200.

Continuing with reference to FIG. 14, at step 1403, a depth map of the image is generated based on the optical flow field of the image and the pose of the imaging unit corresponding to the image. The depth map comprises depths of the object points corresponding to the plurality of pixels. In some embodiments, the step 1403 may be similarly implemented as the step 1203 in the method 1200.

Continuing with reference to FIG. 14, at step 1405, object point spatial coordinates of the object points corresponding to the plurality of pixels are determined based on the depth map of the image and pixel coordinates of the plurality of pixels. In some embodiments, the step 1405 may be similarly implemented as the step 1205 in the method 1200.

Continuing with reference to FIG. 14, at step 1407, color information of the plurality of pixels is obtained based on the image. In some embodiments, the step 1407 may be similarly implemented as the step 1207 in the method 1200.

Continuing with reference to FIG. 14, at step 1409, based on the image, a point cloud fusion is performed on the image based on the color information of the plurality of pixels and the object point spatial coordinates, to generate a three-dimensional point cloud. In some embodiments, the step 1409 may be similarly implemented as the step 1209 in the method 1200.

Figure 15:
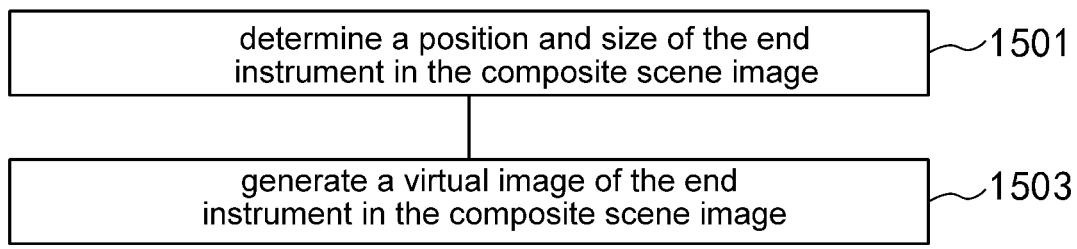
FIG. 15 shows a flowchart of a method of generating a virtual image of the end instrument in the composite scene image according to some embodiments of the present disclosure.

Some embodiments of the present disclosure provide a method of generating a virtual image of the end instrument in a composite scene image. FIG. 15 shows a flowchart of a method 1500 of generating a virtual image of the end instrument in a composite scene image according to some embodiments of the present disclosure. In some embodiments, part or all of the steps in the method 1500 may be performed by the control device (e.g., the control device 500 shown in FIG. 5 or the control device 1770 shown in FIG. 17) of the robot system (e.g., the robot system 100 shown in FIG. 1 or the robot system 1700 shown in FIG. 17). The control device may include a computing device. The method 1500 may be implemented by software, firmware and/or hardware. In some embodiments, the method 1500 may be implemented as computer-readable instructions. These instructions may be read and executed by a general-purpose processor or a dedicated processor (e.g., the control device 1770 shown in FIG. 17). In some embodiments, these instructions may be stored on a computer-readable medium.

Referring to FIG. 15, at step 1501, a position and size of the end instrument in the composite scene image is determined. In some embodiments, the position and size of the end instrument in the composite scene image may be determined based on inherent parameters of the end instrument. The inherent parameters of the end instrument may include a position parameter of the end instrument on the main body (e.g., a relative positional relationship with the first imaging unit and the second imaging unit), an orientation parameter and a size parameter. For example, the inherent parameters of the end instrument may be known or obtained by calibration. In some embodiments, it may also be possible to determine, based on the edges of the first environment image, the second environment image or the supplementary image, the position and size of the end instrument in the composite scene image.

Continuing with reference to FIG. 15, at step 1503, a virtual image of the end instrument is generated in the composite scene image. In some embodiments, the virtual image of the end instrument may be generated in the composite scene image by real-time rendering. For example, the virtual image of the end instrument may be generated for each frame of the composite scene images. In some embodiments, the virtual image of the end instrument may include a contour line and/or a transparent entity illustrating the end instrument. As a result, the position and size of the end instrument can be shown without hindering the operator's field of view.

In some embodiments, the method 6000 may further include in the composite scene image, generating, along an axis direction of the virtual image of the end instrument, a first virtual ruler for indicating a distance. The first virtual ruler may be generated along the contour of the virtual image of the end instrument, and used to show a length of the end instrument, facilitating to improve an accuracy of the operation of the operator. In some embodiments, the method of generating the first virtual ruler may be similarly implemented as the step 1503 in the method 1500.

In some embodiments, the method 6000 may further include determining a distance between the end of the main body and a surgical site, and based on the distance between the end of the main body and the surgical site, updating the first virtual ruler to a second virtual ruler. For example, the distance between the end of the main body and the surgical site may be measured by a ranging unit on the main body, and the second virtual ruler is generated based on this distance. The second virtual ruler may include information indicated by the first virtual ruler and information about the distance between the end of the main body and the surgical site. By updating the first virtual ruler to the second virtual ruler, the length of the end instrument and the distance between the end instrument and the surgical site may be shown simultaneously, helping to further improve an accuracy of the operation of the operator. In some embodiments, the method of generating the second virtual ruler may be similarly implemented as the step 1503 in the method 1500.

In some embodiments of the present disclosure, the present disclosure further provides a computer device comprising a memory and a processor. The memory may be used to store at least one instruction. The processor is coupled to the memory, and is to execute the at least one instruction to perform some or all of the steps of the methods of the present disclosure, such as some or all of the steps of the methods shown in FIG. 6, FIG. 9 and FIGS. 11-15.

FIG. 16 shows a schematic block diagram of a computer device 1600 according to some embodiments of the present disclosure. Referring to FIG. 16, the computer device 1600 may include a central processing unit (CPU) 1601, a system memory 1604 including a random access memory (RAM) 1602 and a read-only memory (ROM) 1603, and a system bus 1605 connecting the various components. The computer device 1600 may further include an input/output system, and a mass storage device 1607 for storing an operating system 1613, application 1614 and other program modules 1615. The input/output device comprises an input/output control device 1610 mainly comprising a display 1608 and an input device 1609.

The mass storage device 1607 is connected to the central processing unit 1601 via a mass storage control device (not shown) connected to the system bus 1605. The mass storage device 1607 or a computer-readable medium provides non-volatile storage for the computer device. The mass storage device 1607 may include a computer-readable medium (not shown) such as a hard disk or a Compact Disc Read-Only Memory (CD-ROM) drive or the like.

Without loss of generality, the computer-readable medium may include a computer storage medium and a communication medium. The computer storage medium includes a volatile and non-volatile, removable and non-removable medium implemented by any of methods or technologies for storing information such as computer-readable instructions, data structures, program modules, or other data and the like. The computer storage medium includes RAM, ROM, a flash memory or other solid-state memory technology, CD-ROM, or other optical storage, a tape cartridge, a tape, disk storage, or other magnetic storage devices. Of course, those skilled in the art will know that the computer storage medium are not limited to the above. The above system memory and mass storage device may be collectively referred to as memory.

The computer device 1600 may be connected to a network 1612 via a network interface unit 1611 connected to the system bus 1605.

The system memory 1604 or the mass storage device 1607 is also used to store one or more instructions. The central processor 1601 implements all or part of the steps of the methods in some embodiments of the present disclosure by executing the one or more instructions.

In some embodiments of the present disclosure, the present disclosure further provides a computer-readable storage medium in which at least one instruction is stored. The at least one instruction is executed by the processor to enable the computer to perform some or all of the steps of the methods in some embodiments of the present application, such as some or all of the steps of the methods disclosed in FIG. 6, FIG. 9 and FIGS. 11-15. Examples of the computer-readable storage medium include a memory for computer programs (instructions), e.g., a read-Only Memory (ROM), a Random Access Memory (RAM), a read-only disc (Compact Disc Read-Only Memory, CD-ROM), a tape, a floppy disk, and an optical data storage device.

FIG. 17 shows a schematic diagram of a robot system 1700 according to some embodiments of the present disclosure. In some embodiments of the present disclosure, see FIG. 17, a robot system 1700 comprises: a master manipulator 1710, a control device 1770, a drive device 1780, a slave tool 1720 and a display device 1790. The master manipulator 1710 includes a robotic arm, a handle disposed on the robotic arm, and at least one master manipulator sensor disposed at at least one joint on the robotic arm for obtaining joint information of the at least one joint. In some embodiments, the master manipulator 1710 includes a six-degree-of-freedom robotic arm. One master manipulator sensor is provided at each joint on the six-degree-of-freedom robotic arm, and joint information (e.g., joint angle data) is generated by the master manipulator sensor of each joint. In some embodiments, the master manipulator sensor uses a potentiometer and/or an encoder. An endoscope 1730 is provided on the slave tool 1720. In some embodiments, the slave tool 1720 includes a motion arm 1740, and the endoscope 1730 may be disposed at a distal end of the motion arm 1740. In some embodiments, the endoscope 1730 includes an operating arm 1750 and an endoscope main body 1760 disposed at an end of the operating arm 1750. A first imaging unit 1761, a second imaging unit 1762, and an end instrument 1765 protruding from a distal end of the main body are provided on the endoscope main body 1760. The first imaging unit 1761 is used to take a first image, the second imaging unit 1762 is used to take a second image, and the end instrument 1765 is used to perform surgical tasks. The display device 1790 is used to display a picture output by the endoscope 1730. The control device 1770 is configured to be connected with the motion arm 1740 and the drive device 1780 to control the motion of the endoscope 1730, and communicatively connected with the endoscope 1730 to process the image output by the endoscope 1730. The control device 1770 is used to perform some or all of the steps of the methods of some embodiments of the present disclosure, such as some or all of the steps of the methods disclosed in FIG. 6, FIG. 9 and FIGS. 11-15.

Note that the above are only exemplary embodiments of the present disclosure and the applied technical principles. Those skilled in the art will appreciate that the present disclosure is not limited to specific embodiments herein, and those skilled in the art can make various apparent changes, readjustments and substitutions without departing from the scope of protection of the present disclosure. Thus, although the present disclosure is described in more detail by the above embodiments, the present disclosure is not limited to the above embodiments. Without departing from the concept of the present disclosure, more other equivalent embodiments may be included, and the scope of the present disclosure is determined by the scope of the appended claims.

What is claimed is:

1. An endoscope master-slave motion control method, wherein the endoscope comprises an operating arm, a main body disposed at an end of the operating arm, a first imaging unit, a second imaging unit, and an end instrument protruding from a distal end of the main body, the method comprises:
   determining a current pose of a master manipulator;
   determining, based on the current pose of the master manipulator and a pose relationship between the master manipulator and the end of the operating arm, a target pose of the end of the operating arm;
   generating, based on the target pose, a drive instruction for driving the end of the operating arm;
   obtaining a first image from the first imaging unit;
   obtaining a second image from the second imaging unit, wherein the first image and the second image have different fields of view and include images of the end instrument;
   generating, based on the first image and the second image, a composite scene image to remove an actual image of the end instrument; and
   generating a virtual image of the end instrument in the composite scene image.

2. The method according to claim 1, further comprising:
   generating, based on the first image and/or the second image, an actual scene image to display an actual image of the end instrument; and
   displaying, in response to a display mode instruction, the composite scene image with the virtual image and/or the actual scene image.

3. The method according to claim 2, wherein the display mode instruction comprises at least one of:
   the drive instruction;
   an end instrument operation instruction for controlling an operation of the end instrument; or
   a display mode selection instruction for selecting a display mode,
   the method further comprises at least one of:
   generating, in response to the drive instruction, a first display signal to display at least the composite scene image with the virtual image;
   generating, in response to the end instrument operation instruction, a second display signal to display at least the actual scene image; or
   generating, in response to the display mode selection instruction, a display signal corresponding to the selected display mode.

4. The method according to claim 3, wherein the drive instruction comprises a retreat instruction for controlling the endoscope to retreat;
   the method further comprises:
   controlling, based on the retreat instruction, the endoscope to move away from the operating area; and
   generating, in response to a distance of the endoscope away from the operating area exceeding a threshold, a first display signal to display at least the composite scene image with the virtual image.

5. The method according to claim 4, further comprising:
   determining whether a distance for which the endoscope retreats exceeds a threshold; or
   determining whether a cumulated value of an amount of position change of the master manipulator that corresponds to the retreat instruction exceeds a threshold.

6. The method according to claim 3, wherein the drive instruction further comprises an automatic exit instruction;
   the method further comprises:
   controlling, based on the automatic exit instruction, the endoscope to exit from a body; and
   generating, in response to the automatic exit instruction, a first display signal to display at least the composite scene image with the virtual image.

7. The method according to claim 4, wherein a display mode control priority of the display mode instruction comprises at least one of:
   a display mode control priority of the display mode selection instruction being higher than a display mode control priority of the retreat instruction;
   a display mode control priority of the retreat instruction being higher than a display mode control priority of the end instrument operation instruction; or
   a display mode control priority of the end instrument operation instruction being higher than display mode control priorities of other drive instructions in the drive instructions other than the retreat instruction and the automatic exit instruction.

8. The method according to claim 3, wherein the display mode selection instruction comprises at least one of:
   a composite scene display instruction for displaying the composite scene image with the virtual image;
   an actual scene display instruction for displaying the actual scene image; or
   a multi-scene display instruction for displaying at least a portion of the actual scene image in a first window and displaying at least a portion of the composite scene image with the virtual image in a second window.

9. The method according to claim 1, wherein the pose relationship comprises at least one of:
   an amount of position change of the end of the operating arm being equal to or proportional to an amount of position change of the master manipulator; and/or
   an amount of orientation change of the end of the operating arm being equal to or proportional to an amount of orientation change of the master manipulator.

10. The method according to claim 1, further comprising:
    determining a current pose of a handle of the master manipulator relative to a reference coordinate system;
    determining a previous pose of the handle relative to the reference coordinate system;
    determining a starting pose of the end of the operating arm relative to an operating arm base coordinate system; and
    determining a target pose of the end of the operating arm relative to the operating arm base coordinate system based on the previous pose and the current pose of the handle relative to the reference coordinate system, a transformation relationship between a current end coordinate system of the operating arm and the operating arm base coordinate system, and the starting pose of the end of the operating arm relative to the operating arm base coordinate system.

11. The method according to claim 1, further comprising:
    performing a plurality of control cycles, wherein in each control cycle:
    determining a current pose of the master manipulator obtained in a previous round of control cycle as a previous pose of the master manipulator in a current round of control cycle; and
    determining a target pose of the end of the operating arm obtained in the previous round of control cycle as a starting pose of the end of the operating arm in the current round of control cycle.

12. The method according to claim 1, wherein generating the composite scene image comprises:
- determining a supplementary image based on the first image or the second image, the supplementary image comprising a portion of the second image or the first image that is blocked by the end instrument;
- determining a first environment image or a second environment image based on the first image or the second image, wherein the first environment image and the second environment image do not include an image of the end instrument; and
- stitching the first environment image or the second environment image and the supplementary image to generate a stitched image.

13. The method according to claim 12, further comprising: for at least one of the first image, the second image, the first environment image, the second environment image, the supplementary image or the stitched image,
- determining, based on the image and a previous frame image of the image, an optical flow field of the image, the optical flow field comprising optical flows of a plurality of pixels in the image;
- generating a depth map of the image based on the optical flow field of the image and a pose of the imaging unit corresponding to the image, the depth map comprising depths of object points corresponding to the plurality of pixels;
- determining, based on the depth map of the image and pixel coordinates of the plurality of pixels, object point spatial coordinates of object points corresponding to the plurality of pixels;
- acquiring, based on the image, color information of the plurality of pixels; and
- performing a point cloud fusion on the image based on the color information of the plurality of pixels and the object point spatial coordinates, to generate a three-dimensional point cloud.

14. The method according to claim 13, wherein generating a depth map of the image based on the optical flow field of the image and a pose of the imaging unit corresponding to the image comprises:
- determining a focus of the optical flow field based on the optical flow field of the image;
- determining distances between the plurality of pixels and the focus based on the focus of the optical flow field;
- determining velocities of the plurality of pixels in the optical flow field based on the optical flow field of the image;
- determining a velocity of the imaging unit based on the pose of the imaging unit corresponding to the image; and
- determining the depth map of the image based on the distances between the plurality of pixels and the focus, the velocities of the plurality of pixels in the optical flow field, and the velocity of the imaging unit.

15. The method according to claim 13, further comprising:
- determining a pose of the imaging unit based on a target pose of the end of the operating arm and a pose relationship between the end of the operating arm and the imaging unit.

16. The method according to claim 1, further comprising:
- determining a position and size of the end instrument in the composite scene image; and
- generating the virtual image of the end instrument in the composite scene image.

17. The method according to claim 16, wherein,
- the virtual image of the end instrument includes a contour line and/or a transparent entity for illustrating the end instrument; and/or
- in the composite scene image, a first virtual ruler for indicating a distance is generated along an axis direction of the virtual image of the end instrument.

18. The method according to claim 17, further comprising:
- determining a distance between the endoscope and a surgical site; and
- updating the first virtual ruler to a second virtual ruler based on the distance between the endoscope and the surgical site.

19. A non-transitory computer-readable storage medium for storing at least one instruction that when executed by a computer, causes the computer to perform the method according to claim 1.

20. A robotic system, comprising:
- a master manipulator including a robotic arm, a handle disposed on the robotic arm, and at least one master manipulator sensor disposed at at least one joint on the robotic arm for obtaining joint information of the at least one joint;
- an endoscope including an operating arm, a main body disposed at an end of the operating arm, a first imaging unit, a second imaging unit, and an end instrument protruding from a distal end of the main body;
- at least one drive device for driving the operating arm;
- at least one drive device sensor coupled with the at least one drive device and for obtaining status information of the at least one drive device;
- a control device configured to be connected with the master manipulator, the at least one drive device, the at least one drive device sensor, and the endoscope, and perform the method according to claim 1; and
- a display device for displaying an image based on an instruction output by the control device.

* * * * *